United States Patent
Langlois

(10) Patent No.: US 11,607,326 B2
(45) Date of Patent: *Mar. 21, 2023

(54) REACTIVE LAYER CONTROL SYSTEM FOR PROSTHETIC DEVICES

(71) Applicant: VICTHOM LABORATORY INC., Laval (CA)

(72) Inventor: David Langlois, St-Jacques-de Leeds (CA)

(73) Assignee: VICTHOM LABORATORY INC., Laval (CA)

( * ) Notice: Subject to any disclaimer, the term of this patent is extended or adjusted under 35 U.S.C. 154(b) by 509 days.

This patent is subject to a terminal disclaimer.

(21) Appl. No.: 16/533,340

(22) Filed: Aug. 6, 2019

(65) Prior Publication Data
US 2019/0365545 A1    Dec. 5, 2019

Related U.S. Application Data

(60) Continuation of application No. 15/803,154, filed on Nov. 3, 2017, now Pat. No. 10,405,996, which is a (Continued)

(51) Int. Cl.
   A61F 2/70    (2006.01)
   A61F 2/68    (2006.01)
   (Continued)

(52) U.S. Cl.
   CPC .......... *A61F 2/70* (2013.01); *A61F 2/60* (2013.01); *A61F 2/64* (2013.01); *A61F 2/68* (2013.01);
   (Continued)

(58) Field of Classification Search
   CPC ...... A61F 2/70; A61F 2/72; A61F 2/68; A61F 2002/5036; A61F 2002/5038;
   (Continued)

(56) References Cited

U.S. PATENT DOCUMENTS

| | | |
|---|---|---|
| 909,859 A | 1/1909 | Apgar |
| 2,475,373 A | 7/1949 | Catranis |

(Continued)

FOREIGN PATENT DOCUMENTS

| | | |
|---|---|---|
| CA | 2 405 356 | 10/2001 |
| CA | 2 494 365 | 3/2004 |

(Continued)

OTHER PUBLICATIONS

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

(Continued)

*Primary Examiner* — Christie L Bahena
(74) *Attorney, Agent, or Firm* — Knobbe, Martens, Olson & Bear, LLP

(57) ABSTRACT

A variable gain impedance controller for use in a control system for controlling a motorized prosthetic or orthotic apparatus provided with a joint. The controller comprises a sensor input for receiving a signal indicative of an interaction between the apparatus and the ground, a torque sensor input for receiving a signal indicative of the torque at the joint, and a variable gain scheduler in communication with the sensor input to receive data therefrom thereby providing a variable torque gain. The variable gain impedance controller adjusts its control on the apparatus based on the variable torque gain and the indicated torque to increase the joint resistance to motion when the signal received from the sensor input indicates an interaction between the apparatus and the ground, and decrease the joint resistance to motion when the signal received from the sensor input indicates an absence of interaction between the apparatus and the ground.

17 Claims, 8 Drawing Sheets

Related U.S. Application Data division of application No. 12/523,710, filed as application No. PCT/CA2008/000110 on Jan. 21, 2008, now Pat. No. 9,808,357.

(60) Provisional application No. 60/881,168, filed on Jan. 19, 2007.

(51) Int. Cl.
  A61F 2/64 (2006.01)
  A61F 2/60 (2006.01)
  A61F 2/50 (2006.01)
  A61F 2/76 (2006.01)

(52) U.S. Cl.
  CPC .......... A61F 2002/5033 (2013.01); A61F 2002/6818 (2013.01); A61F 2002/701 (2013.01); A61F 2002/704 (2013.01); A61F 2002/762 (2013.01); A61F 2002/764 (2013.01); A61F 2002/7625 (2013.01); A61F 2002/7635 (2013.01); A61F 2002/7645 (2013.01)

(58) Field of Classification Search
  CPC ........ A61F 2002/6818; A61F 2002/745; A61F 2005/0155; A61F 2005/0169; G05B 19/358; G05B 19/378; B25J 9/0006
  See application file for complete search history.

(56) References Cited

U.S. PATENT DOCUMENTS

| | | |
|---|---|---|
| 2,568,051 A | 9/1951 | Catranis |
| 3,557,387 A | 1/1971 | Ohlenbusch et al. |
| 3,589,134 A | 6/1971 | Hackmann |
| 3,871,032 A | 3/1975 | Karas |
| 3,953,900 A | 5/1976 | Thompson |
| 3,995,324 A | 12/1976 | Burch |
| 4,030,141 A | 6/1977 | Graupe |
| 4,172,433 A * | 10/1979 | Bianchi ............ F02D 41/1487 123/436 |
| 4,179,759 A | 12/1979 | Smith |
| 4,209,860 A | 7/1980 | Graupe |
| 4,387,472 A | 6/1983 | Wilson |
| 4,398,109 A | 8/1983 | Kuwako et al. |
| 4,488,320 A | 12/1984 | Wilson |
| 4,521,924 A | 6/1985 | Jacobsen et al. |
| 4,558,704 A | 12/1985 | Petrofsky |
| 4,579,558 A | 4/1986 | Ramer |
| 4,652,266 A | 3/1987 | Truesdell |
| 4,776,852 A | 10/1988 | Rubic |
| 4,805,455 A | 2/1989 | DelGiorno et al. |
| 4,994,086 A | 2/1991 | Edwards |
| 5,020,790 A | 6/1991 | Beard et al. |
| 5,062,673 A | 11/1991 | Mimura |
| 5,062,856 A | 11/1991 | Sawamura et al. |
| 5,062,857 A | 11/1991 | Berringer |
| 5,101,472 A | 3/1992 | Repperger |
| 5,116,384 A | 5/1992 | Wilson et al. |
| 5,156,630 A | 10/1992 | Rappoport et al. |
| 5,200,679 A | 4/1993 | Graham |
| 5,201,772 A | 4/1993 | Maxwell |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe et al. |
| 5,282,460 A | 2/1994 | Boldt |
| 5,376,138 A | 12/1994 | Bouchard et al. |
| 5,376,141 A | 12/1994 | Phillips |
| 5,383,939 A | 1/1995 | James |
| 5,406,845 A | 4/1995 | Berger et al. |
| 5,413,611 A | 5/1995 | Haslam, II et al. |
| 5,425,780 A | 6/1995 | Flatt et al. |
| 5,430,643 A | 7/1995 | Seraji |
| 5,443,528 A | 8/1995 | Allen |
| 5,455,497 A | 10/1995 | Hirose et al. |
| 5,484,389 A | 1/1996 | Stark et al. |
| 5,486,209 A | 1/1996 | Phillips |
| 5,571,205 A | 11/1996 | James |
| 5,571,210 A | 11/1996 | Lindh |
| 5,571,213 A | 11/1996 | Allen |
| 5,650,704 A | 7/1997 | Pratt et al. |
| 5,662,693 A | 9/1997 | Johnson et al. |
| 5,695,527 A | 12/1997 | Allen |
| 5,704,946 A | 1/1998 | Greene |
| 5,725,598 A | 3/1998 | Phillips |
| 5,746,774 A | 5/1998 | Kramer |
| 5,779,735 A | 7/1998 | Molino |
| 5,800,570 A | 9/1998 | Collier |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 5,929,332 A | 7/1999 | Brown |
| 5,948,021 A | 9/1999 | Radcliffe |
| 5,954,621 A | 9/1999 | Joutras et al. |
| 5,957,981 A | 9/1999 | Gramnaes |
| 5,984,972 A | 11/1999 | Huston et al. |
| 6,007,582 A | 12/1999 | May |
| 6,029,374 A | 2/2000 | Herr et al. |
| 6,061,577 A | 5/2000 | Andrieu et al. |
| 6,071,313 A | 6/2000 | Phillips |
| 6,086,616 A | 7/2000 | Okuda et al. |
| 6,091,977 A | 7/2000 | Tarjan et al. |
| 6,113,642 A | 9/2000 | Petrofsky et al. |
| 6,117,177 A | 9/2000 | Chen et al. |
| 6,122,960 A | 9/2000 | Hutchings et al. |
| 6,129,766 A | 10/2000 | Johnson et al. |
| 6,187,052 B1 | 2/2001 | Molino et al. |
| 6,206,932 B1 | 3/2001 | Johnson |
| 6,361,570 B1 | 3/2002 | Gow |
| 6,378,190 B2 | 4/2002 | Akeel |
| 6,379,393 B1 | 4/2002 | Mavroidis et al. |
| 6,423,098 B1 | 7/2002 | Biedermann |
| 6,425,925 B1 | 7/2002 | Grundei |
| 6,436,149 B1 | 8/2002 | Rincoe |
| 6,443,993 B1 | 9/2002 | Koniuk |
| 6,482,236 B2 | 11/2002 | Habecker |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,503 B1 | 2/2003 | Naft et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,543,987 B2 | 4/2003 | Ehrat |
| 6,587,728 B2 | 7/2003 | Fang et al. |
| 6,610,101 B2 | 8/2003 | Herr et al. |
| 6,613,097 B1 | 9/2003 | Cooper |
| 6,645,252 B2 | 11/2003 | Asai et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,719,807 B2 | 4/2004 | Harris |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,770,045 B2 | 8/2004 | Naft et al. |
| 6,813,582 B2 | 11/2004 | Levi et al. |
| 6,824,569 B2 | 11/2004 | Okediji |
| 6,863,695 B2 | 3/2005 | Doddroe et al. |
| 6,875,241 B2 | 4/2005 | Christensen |
| 6,908,488 B2 | 6/2005 | Paasivaara et al. |
| 6,910,331 B2 | 6/2005 | Asai et al. |
| 6,918,308 B2 | 7/2005 | Biedermann |
| 6,955,692 B2 | 10/2005 | Grundei |
| 6,966,882 B2 | 11/2005 | Horst |
| 6,969,408 B2 | 11/2005 | Lecomte et al. |
| 7,029,500 B2 | 4/2006 | Martin |

(56) References Cited

U.S. PATENT DOCUMENTS

| | | |
|---|---|---|
| 7,066,964 B2 | 6/2006 | Wild |
| 7,112,938 B2 | 9/2006 | Takenaka et al. |
| 7,118,601 B2 | 10/2006 | Yasui |
| 7,137,998 B2 | 11/2006 | Bédard et al. |
| 7,147,667 B2 | 12/2006 | Bédard et al. |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,198,071 B2 | 4/2007 | Bisbee, III et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bédard et al. |
| 7,347,877 B2 | 3/2008 | Clausen et al. |
| 7,381,192 B2 | 6/2008 | Brodard et al. |
| 7,396,337 B2 | 7/2008 | McBean et al. |
| 7,410,471 B1 | 8/2008 | Campbell et al. |
| 7,455,696 B2 | 11/2008 | Bisbee, III et al. |
| 7,462,201 B2 | 12/2008 | Christensen |
| 7,475,606 B2 | 1/2009 | Selig et al. |
| 7,485,152 B2 | 2/2009 | Haynes et al. |
| 7,500,407 B2 | 3/2009 | Boiten |
| 7,520,904 B2 | 4/2009 | Christensen |
| 7,531,006 B2 | 5/2009 | Clausen et al. |
| 7,544,172 B2 * | 6/2009 | Santos-Munne ....... A61H 3/008 601/5 |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,597,017 B2 | 10/2009 | Bédard et al. |
| 7,602,301 B1 | 10/2009 | Stirling et al. |
| 7,611,543 B2 | 11/2009 | Townsend et al. |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,794,505 B2 | 9/2010 | Clausen et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,846,213 B2 | 12/2010 | Lecomte et al. |
| 7,862,620 B2 | 1/2011 | Clausen et al. |
| 7,867,284 B2 | 1/2011 | Bédard et al. |
| 7,867,285 B2 | 1/2011 | Clausen et al. |
| 7,918,808 B2 | 4/2011 | Simmons |
| 7,942,935 B2 | 5/2011 | Iversen et al. |
| 7,953,549 B2 | 5/2011 | Graham et al. |
| 7,955,398 B2 | 6/2011 | Bédard et al. |
| 7,985,265 B2 | 7/2011 | Moser et al. |
| 7,992,849 B2 | 8/2011 | Sugar et al. |
| 8,011,229 B2 | 9/2011 | Lieberman et al. |
| RE42,903 E | 11/2011 | Deffenbaugh et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,122,772 B2 | 2/2012 | Clausen et al. |
| 8,142,370 B2 | 3/2012 | Weinberg et al. |
| 8,231,687 B2 | 7/2012 | Bédard et al. |
| 8,323,354 B2 | 12/2012 | Bédard et al. |
| 8,366,788 B2 | 2/2013 | Moser et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,480,760 B2 | 7/2013 | Hansen et al. |
| 8,500,823 B2 | 8/2013 | Herr et al. |
| 8,512,415 B2 | 8/2013 | Herr et al. |
| 8,551,184 B1 | 10/2013 | Herr |
| 8,555,715 B2 | 10/2013 | Langlois et al. |
| 7,431,737 C1 | 12/2013 | Ragnarsdottir et al. |
| 8,601,897 B2 | 12/2013 | Lauzier et al. |
| 8,617,254 B2 | 12/2013 | Bisbee, III et al. |
| 8,652,218 B2 | 2/2014 | Goldfarb et al. |
| 8,657,886 B2 | 2/2014 | Clausen et al. |
| 8,702,811 B2 | 4/2014 | Ragnarsdottir et al. |
| 8,709,097 B2 | 4/2014 | Jonsson et al. |
| 7,896,927 C1 | 5/2014 | Clausen et al. |
| 8,764,850 B2 | 7/2014 | Hanset et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,869,626 B2 | 10/2014 | Clausen et al. |
| 8,870,967 B2 | 10/2014 | Herr et al. |
| 8,888,864 B2 | 11/2014 | Iversen et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 10,195,057 B2 | 2/2019 | Clausen |
| 10,251,762 B2 | 4/2019 | Langlois |
| 10,299,943 B2 | 5/2019 | Clausen et al. |
| 10,307,271 B2 | 6/2019 | Holgate et al. |
| 10,369,019 B2 | 8/2019 | Clausen et al. |
| 10,390,974 B2 | 8/2019 | Clausen et al. |
| 10,405,996 B2 | 9/2019 | Langlois |
| 10,543,109 B2 | 1/2020 | Holgate |
| 10,575,970 B2 | 3/2020 | Holgate |
| 10,695,197 B2 | 6/2020 | Clausen |
| 10,940,027 B2 | 3/2021 | Langlois et al. |
| 11,007,072 B2 | 5/2021 | Gilbert et al. |
| 2001/0002772 A1 | 6/2001 | Kim et al. |
| 2001/0020143 A1 | 9/2001 | Stark et al. |
| 2001/0029400 A1 | 10/2001 | Deffenbaugh et al. |
| 2002/0007690 A1 | 1/2002 | Song et al. |
| 2002/0052663 A1 | 5/2002 | Herr et al. |
| 2002/0079857 A1 | 6/2002 | Ishii et al. |
| 2002/0094919 A1 | 7/2002 | Rennex et al. |
| 2002/0198604 A1 | 12/2002 | Schulman et al. |
| 2003/0005786 A1 | 1/2003 | Stuart et al. |
| 2004/0064195 A1 | 4/2004 | Herr |
| 2004/0078299 A1 | 4/2004 | Down-Logan et al. |
| 2004/0086240 A1 | 5/2004 | Togami et al. |
| 2004/0153484 A1 | 8/2004 | Unno |
| 2004/0169112 A1 | 9/2004 | Grossart |

(56) References Cited

U.S. PATENT DOCUMENTS

| | | |
|---|---|---|
| 2004/0193286 A1 | 9/2004 | Grundei |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0071017 A1 | 3/2005 | Lecomte et al. |
| 2005/0107889 A1 | 5/2005 | Bédard et al. |
| 2005/0113973 A1 | 5/2005 | Endo et al. |
| 2005/0137717 A1 | 6/2005 | Gramnaes |
| 2005/0166685 A1 | 8/2005 | Boiten |
| 2005/0197717 A1 | 9/2005 | Ragnarsdottir et al. |
| 2005/0216097 A1 | 9/2005 | Rifkin |
| 2005/0251079 A1 | 11/2005 | Carvey et al. |
| 2005/0283257 A1 | 12/2005 | Bisbee et al. |
| 2006/0025959 A1 | 2/2006 | Gomez et al. |
| 2006/0069336 A1 | 3/2006 | Krebs et al. |
| 2006/0135883 A1 | 6/2006 | Jónsson et al. |
| 2006/0136072 A1 | 6/2006 | Bisbee et al. |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0016329 A1 | 1/2007 | Herr et al. |
| 2007/0032748 A1 | 2/2007 | McNeil et al. |
| 2007/0043449 A1 | 2/2007 | Herr et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1 | 1/2008 | Mosier |
| 2008/0033578 A1 | 2/2008 | Christensen |
| 2008/0046096 A1 | 2/2008 | Bédard et al. |
| 2008/0058668 A1 | 3/2008 | Seyed Momen et al. |
| 2008/0133171 A1 | 6/2008 | Feichtinger et al. |
| 2008/0141813 A1 | 6/2008 | Ehrat |
| 2008/0262635 A1 | 10/2008 | Moser et al. |
| 2008/0306612 A1 | 12/2008 | Mosler |
| 2009/0030530 A1 | 1/2009 | Martin |
| 2009/0054996 A1 | 2/2009 | Sykes et al. |
| 2009/0056445 A1 | 3/2009 | Veltink |
| 2009/0082869 A1 | 3/2009 | Slemker et al. |
| 2009/0088912 A1 | 4/2009 | Rajaraman |
| 2009/0171469 A1 | 7/2009 | Thorsteinsson et al. |
| 2009/0192625 A1 | 7/2009 | Boiten |
| 2009/0204229 A1 | 8/2009 | Mosley et al. |
| 2009/0204230 A1 | 8/2009 | Kaltenborn et al. |
| 2009/0265018 A1 | 10/2009 | Goldfarb et al. |
| 2009/0312844 A1 | 12/2009 | Ikeuchi et al. |
| 2010/0023133 A1 | 1/2010 | Fairbanks et al. |
| 2010/0030343 A1 | 2/2010 | Hansen et al. |
| 2010/0042228 A1 | 2/2010 | Doddroe et al. |
| 2010/0042256 A1 | 2/2010 | Takenaka et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0185301 A1 | 7/2010 | Hansen et al. |
| 2010/0241242 A1 | 9/2010 | Herr et al. |
| 2010/0262260 A1 | 10/2010 | Bédard et al. |
| 2010/0275718 A1 | 11/2010 | Stuart et al. |
| 2010/0286796 A1 | 11/2010 | Clausen |
| 2010/0324456 A1 | 12/2010 | Jónsson et al. |
| 2010/0324698 A1 | 12/2010 | Sverrisson et al. |
| 2010/0324699 A1 | 12/2010 | Herr et al. |
| 2011/0015761 A1 | 1/2011 | Celebi et al. |
| 2011/0082566 A1 | 4/2011 | Herr et al. |
| 2011/0106274 A1 | 5/2011 | Ragnarsdottir et al. |
| 2011/0130847 A1 | 6/2011 | Bédard et al. |
| 2011/0132131 A1 | 6/2011 | Worz |
| 2011/0137429 A1 | 6/2011 | Bédard et al. |
| 2011/0166674 A1 | 7/2011 | Montmartin |
| 2011/0196509 A1 | 8/2011 | Jansen et al. |
| 2011/0202144 A1 | 8/2011 | Palmer et al. |
| 2011/0208322 A1 | 8/2011 | Rifkin et al. |
| 2011/0224804 A1 | 9/2011 | Clausen et al. |
| 2011/0264230 A1 | 10/2011 | Herr et al. |
| 2011/0295384 A1 | 12/2011 | Herr et al. |
| 2011/0295385 A1 | 12/2011 | Herr et al. |
| 2012/0016492 A1 | 1/2012 | Clausen |
| 2012/0078415 A1 | 3/2012 | Kubo et al. |
| 2012/0083901 A1 | 4/2012 | Langlois et al. |
| 2012/0130508 A1 | 5/2012 | Harris et al. |
| 2012/0203359 A1 | 8/2012 | Schimmels et al. |
| 2012/0209405 A1 | 8/2012 | Herr et al. |
| 2012/0226364 A1 | 9/2012 | Kampas et al. |
| 2012/0259430 A1 | 10/2012 | Han et al. |
| 2012/0283844 A1 | 11/2012 | Langlois |
| 2012/0283845 A1 | 11/2012 | Herr et al. |
| 2012/0330439 A1 | 12/2012 | Goldfarb et al. |
| 2013/0035769 A1 | 2/2013 | Bédard et al. |
| 2013/0095861 A1 | 4/2013 | Li et al. |
| 2013/0118287 A1 | 5/2013 | Holgate |
| 2013/0142608 A1 | 6/2013 | Zhang et al. |
| 2013/0144402 A1 | 6/2013 | Clausen et al. |
| 2013/0173022 A1 | 7/2013 | Arabian et al. |
| 2013/0197408 A1 | 8/2013 | Goldfarb et al. |
| 2013/0204395 A1 | 8/2013 | Gramnaes |
| 2013/0218295 A1 | 8/2013 | Holgate et al. |
| 2013/0218298 A1 | 8/2013 | Mosler |
| 2013/0261766 A1 | 10/2013 | Langlois et al. |
| 2013/0268093 A1 | 10/2013 | Gilbert et al. |
| 2013/0282141 A1 | 10/2013 | Herr et al. |
| 2013/0297041 A1 | 11/2013 | Bédard |
| 2013/0310949 A1 | 11/2013 | Goldfarb et al. |
| 2013/0311133 A1 | 11/2013 | Kordari et al. |
| 2013/0311134 A1 | 11/2013 | Kordari et al. |
| 2014/0039642 A1 | 2/2014 | Nijiman et al. |
| 2014/0074243 A1 | 3/2014 | Holgate |
| 2014/0081424 A1 | 3/2014 | Herr et al. |
| 2014/0114437 A1 | 4/2014 | Herr et al. |
| 2014/0121782 A1 | 5/2014 | Herr et al. |
| 2014/0156025 A1 | 6/2014 | Bisbee, III et al. |
| 2014/0191522 A1 | 7/2014 | Birglen |
| 2014/0200680 A1 | 7/2014 | Holgate et al. |
| 2014/0243997 A1 | 8/2014 | Clausen et al. |
| 2014/0277586 A1 | 9/2014 | Clausen |
| 2014/0330393 A1 | 11/2014 | Ward et al. |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0223952 A1 | 8/2015 | Langlois |
| 2015/0265429 A1 | 9/2015 | Jónsson et al. |
| 2015/0297368 A1 | 10/2015 | Langlois |
| 2015/0320573 A1 | 11/2015 | Gramnaes |
| 2015/0328020 A1 | 11/2015 | Clausen et al. |
| 2016/0158031 A1 | 6/2016 | Ward et al. |
| 2016/0158032 A1 | 6/2016 | Ward et al. |
| 2016/0242938 A1 | 8/2016 | Holgate |
| 2016/0302956 A1 | 10/2016 | Gilbert et al. |
| 2017/0049659 A1 | 2/2017 | Farris et al. |
| 2017/0071762 A1 | 3/2017 | Holgate et al. |
| 2017/0095355 A1 | 4/2017 | Holgate |
| 2017/0112640 A1 | 4/2017 | Clausen et al. |
| 2017/0241497 A1 | 8/2017 | Mooney et al. |
| 2017/0304083 A1 | 10/2017 | Clausen |
| 2017/0340504 A1 | 11/2017 | Sanz Merodio et al. |
| 2018/0125678 A1 | 5/2018 | Langlois |
| 2018/0177618 A1 | 6/2018 | Langlois |
| 2019/0175369 A1 | 6/2019 | Langlois |
| 2019/0224026 A1 | 7/2019 | Clausen |
| 2020/0000611 A1 | 1/2020 | Clausen et al. |
| 2020/0214856 A1 | 7/2020 | Hogate |
| 2020/0383804 A1 | 12/2020 | Clausen |

FOREIGN PATENT DOCUMENTS

| | | |
|---|---|---|
| CA | 2 543 061 | 6/2005 |
| CA | 2 546 858 | 6/2005 |
| CH | 543 277 | 12/1973 |
| CN | 2043873 U | 9/1989 |

(56) References Cited

FOREIGN PATENT DOCUMENTS

| | | |
|---|---|---|
| CN | 1074109 | 7/1993 |
| CN | 1215614 | 5/1999 |
| CN | 2400072 Y | 10/2000 |
| CN | 1376856 | 10/2002 |
| CN | 2776340 | 5/2006 |
| CN | 1929797 | 3/2007 |
| DE | 39 23 057 | 1/1991 |
| DE | 42 29 330 | 3/1994 |
| EP | 0 358 056 | 3/1990 |
| EP | 0 380 060 | 8/1990 |
| EP | 0 549 855 | 7/1993 |
| EP | 1 166 726 | 1/2002 |
| EP | 1 169 982 | 1/2002 |
| EP | 1 410 780 | 4/2004 |
| EP | 1 442 704 | 8/2004 |
| EP | 1 547 567 | 6/2005 |
| EP | 1 792 597 | 6/2007 |
| EP | 2 702 963 | 3/2014 |
| FR | 2 293 185 | 7/1976 |
| FR | 2 623 086 | 5/1989 |
| FR | 2 816 463 | 5/2002 |
| GB | 2 201 260 | 8/1988 |
| GB | 2 228 201 | 8/1990 |
| GB | 2 260 495 | 4/1993 |
| GB | 2 301 776 | 12/1996 |
| GB | 2 302 949 | 2/1997 |
| GB | 2 367 753 | 4/2002 |
| JP | 59-032453 | 2/1984 |
| JP | 59-071747 | 4/1984 |
| JP | 59-088147 | 5/1984 |
| JP | 59-189843 | 10/1984 |
| JP | 60-177102 | 9/1985 |
| JP | 05-123348 | 5/1993 |
| JP | 05-161668 | 6/1993 |
| JP | 07-024766 | 1/1995 |
| JP | 11-056885 | 3/1999 |
| JP | 11-215793 | 8/1999 |
| JP | 2001-277175 | 10/2001 |
| JP | 2002-191654 | 7/2002 |
| JP | 2005-536317 | 12/2005 |
| JP | 2009-153660 | 7/2009 |
| KR | 2002-0041137 | 6/2002 |
| SU | 1447366 | 12/1988 |
| SU | 1731210 | 5/1992 |
| WO | WO 94/009727 | 5/1994 |
| WO | WO 96/041599 | 12/1996 |
| WO | WO 97/027822 | 8/1997 |
| WO | WO 99/008621 | 2/1999 |
| WO | WO 00/027318 | 5/2000 |
| WO | WO 00/038599 | 7/2000 |
| WO | WO 01/072245 | 10/2001 |
| WO | WO 03/003953 | 1/2003 |
| WO | WO 03/088373 | 10/2003 |
| WO | WO 2004/017873 | 3/2004 |
| WO | WO 2004/017890 | 3/2004 |
| WO | WO 2005/079712 | 9/2005 |
| WO | WO 2005/087144 | 9/2005 |
| WO | WO 2005/110293 | 11/2005 |
| WO | WO 2006/024876 | 3/2006 |
| WO | WO 2006/076164 | 7/2006 |
| WO | WO 2006/083913 | 8/2006 |
| WO | WO 2006/088966 | 8/2006 |
| WO | WO 2007/025116 | 3/2007 |
| WO | WO 2007/027668 | 3/2007 |
| WO | WO 2007/095933 | 8/2007 |
| WO | WO 2008/080231 | 7/2008 |
| WO | WO 2008/086629 | 7/2008 |
| WO | WO 2010/027968 | 3/2010 |
| WO | WO 2010/129716 | 11/2010 |
| WO | WO 2010/148134 | 12/2010 |
| WO | WO 2011/005482 | 1/2011 |
| WO | WO 2011/096965 | 8/2011 |
| WO | WO 2012/006462 | 1/2012 |
| WO | WO 2012/047721 | 4/2012 |
| WO | WO 2012/062279 | 5/2012 |
| WO | WO 2012/091555 | 7/2012 |
| WO | WO 2012/150500 | 11/2012 |
| WO | WO 2013/006585 | 1/2013 |
| WO | WO 2013/148726 | 10/2013 |
| WO | WO 2014/133975 | 9/2014 |
| WO | WO 2014/159114 | 10/2014 |
| WO | WO 2015/157723 | 10/2015 |

OTHER PUBLICATIONS

Dietl et al., "Der Einsatz von Elektronik bei Prothesen zur Versorgung der unteren Extremität," Med. Orth. Tech., 1997, vol. 117, pp. 31-35.
Diginfo TV, "Powered Prosthetic Thigh and Leg", uploaded Nov. 7, 2008 http://www.youtube.com/watch?v=lqjtTzNEd54&feature=youtu.be%3E [Screenshots retrieved Oct. 23, 2014 in 9 pages].
"Extension Spring Design Theory, Spring Rate of Extension Springs," http://web.archive.org/web/20131209120508/http://springipedia.com/extension-desion-theory.asp as archived Dec. 9, 2013 in 1 page.
Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.
Herr et al., "Patient-Adaptive Prosthetic and Orthotic Leg Systems," In Proceedings of the 12th Nordic Baltic Conference on Biomedical Engineering and Medical Physics, Jun. 18-22, 2002, pp. 18-21.
International Preliminary Report on Patentability and Written Opinion in International Application No. PCT/CA2008/000110, dated Jul. 21, 2009 in 7 pages.
International Search Report in International Application No. PCT/CA2003/000937 dated Dec. 3, 2003 in 4 pages.
International Search Report in International Application No. PCT/CA2008/000110, dated May 7, 2008 in 4 pages.
Official Communication in Canadian Application No. 2,676,067, dated Mar. 1, 2016.
Official Communication in Canadian Application No. 2,676,067, dated Mar. 10, 2015.
Official Communication in European Application No. 08706257.6, dated Apr. 24, 2015.
Official Communication in European Application No. 08706257.6, dated Nov. 5, 2013.
Official Communication in European Application No. 03792057.6, dated Mar. 5, 2013.
Lelas et al., "Hydraulic Versus Magnetorheological-Based Electronic Knee Prostheses: A Clinical Comparison," Massachusetts, 2004, pp. 1-16.
Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to constitute prior art to U.S. Pat. No. 7,431,737 and U.S. Pat. No. 7,896,927. Applicant requests that the Examiner to consider this reference as qualifying as prior art to the present application, but reserves the right to challenge the reference's prior art status at a later date.
Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.
Robinson et al., "Series Elastic Actuator Development for a Biomimetic Walking Robot," MIT Leg Laboratory, 1999, pp. 1-8.
Townsend et al., "Biomechanics and Modeling of Bipedal Climbing and Descending," Journal of Biomechanics, vol. 9, No. 4, 1976, pp. 227-239.

* cited by examiner

REACTIVE LAYER CONTROL SYSTEM FOR PROSTHETIC DEVICES

CROSS-REFERENCE TO RELATED APPLICATION

The present application is a continuation of U.S. patent application Ser. No. 15/803,154, filed Nov. 3, 2017, entitled "Reactive Layer Control System For Prosthetic And Orthotic Devices," which is a divisional of U.S. patent application Ser. No. 12/523,710, filed Feb. 2, 2011, entitled "Reactive Layer Control System For Prosthetic And Orthotic Devices," which is a U.S. national stage application of International Patent Application No. PCT/CA2008/000110, filed Jan. 1, 2007, entitled "Reactive Layer Control System For Prosthetic And Orthotic Devices," which claims priority benefit to U.S. Provisional Pat. App. No. 60/881,168, filed Jan. 19, 2007, each of which is hereby incorporated by reference.

TECHNICAL FIELD

The present invention relates to a reactive layer control system for prosthetic and orthotic devices.

BACKGROUND

Prosthetic and orthotic devices for restoring or replacing lost lower-limb functions have been available for many years. Until recently, both types of devices were found as purely mechanical linkages making advantageous usage of simple mechanisms in order to preclude knee buckling in level walking stance phase, while still ensuring some form of swing motion during the aerial phase. While this type of device was shown to be fairly efficient in restoring the structural aspects of the lower-limb role in gait, their incapacity to properly sustain the wide variety of lower-limb dynamics associated with the various gait locomotion activities performed on a daily basis appeared as a sufficient limitation to sustain the development of more advanced devices.

While significant efforts were directed towards designing more advanced mechanisms allowing easier adjustment, or more progressive action, through pneumatics and hydraulics, the rapid advances in energy storage and computer technologies soon allowed to extend the realm of capacities associated with typical orthotic and prosthetic devices. Real-time configuration of passive braking devices such as disclosed, for example, in U.S. Pat. No. 5,383,939 and US Patent Application Publication No. 2006/0136072 A1, greatly improved the adaptability of prosthetic devices to user gait specificities or to variations of the environment in which the locomotion tasks are performed. Moreover, these prosthetic devices allowed the addressing of energy dissipative locomotion tasks in a physiologically-compliant manner never seen before. Although showing increased performance and dynamic adaptation with respect to the locomotion tasks being undertaken when compared to their predecessors, this first generation of computer-controlled prosthetic devices still lacked the adaptability and flexibility required to smoothly integrate into users daily lives.

Integration of computer controls to the prosthetic and orthotic devices brought about the necessity for some sort of control system in order to link sensory inputs to the now dynamically configurable actuator. However, the purely dissipative nature of these devices greatly simplifies the problem as mechanical power exchanges between the user and the device are unidirectional (i.e., user has to initiate all tasks and provide mechanical power).

Latest efforts in the field of advanced orthotic and prosthetic devices, such as disclosed, for example, in US Patent Application Publication No. 2004/0181289 A1, partly resolved some of the limitations observed in the first generation of computer-controlled orthotic and prosthetic devices by providing a fully motorized prosthetic platform, allowing to address all major locomotion tasks, irrespective of their generative or dissipative nature. Requirements for computer-controlled system appeared quite more complex as the interactions between the user and the prosthetic or orthotic device were no longer solely initiated by the user himself. Through the use of a two layer control system, the motorized prosthetic or orthotic device allowed to efficiently manage the mechanical power exchange between the user and the device, such that the synergy between user and motorized prosthetic or orthotic device globally benefited the user. Adequate usage of the prosthetic or orthotic device capacity to generate mechanical power was observed to lead to increased gait quality and activity levels.

Nevertheless, the use of strict state machines to implement the artificial intelligence engine as the highest layer of the prosthetic or orthotic device control system is observed to impose a certain formalism on the manner in which the user executes typical locomotion tasks. While generating a certain learning burden on the user side, the use of firm triggers in order to trigger either distinct state transition or specific joint behavior greatly affects man-machine symbiosis. Moreover, limitations associated with the use of a strict state machine artificial intelligence engine when working in a highly variable environment (i.e., external environment and user himself) are well known and quickly show up as robustness issues from a system perspective. Finally, processing associated with the extraction of complex features associated with specific locomotion task detection is also known to generate a latency between measurement of the sensors value and implementation of the actual actions, which is often observed to greatly affect the prosthetic or orthotic device usability and performance.

Furthermore, common prosthetic or orthotic devices lack the ability to properly reproduce natural knee joint behavior and dynamic properties when used in a context that significantly differs from typical locomotion tasks. While generation of proper joint dynamics during cyclical locomotion portions ensure high symbiosis and user benefits, limitations observed in the capacity to reproduce natural joint compliance, or motions, in either non-locomotor or non-cyclical tasks significantly affect orthotic, or prosthetic, device usability and, accordingly, associated user benefits.

Based on these last observations, it clearly appears that requirements for an improved orthotic and prosthetic control system exist. More specifically, a need to develop a control system architecture and associated engines that are able to sustain more efficiently limited ambulation, as well as non-cyclical and cyclical gait for users suffering of either amputation of the lower-limb or dysfunction requiring the use of an orthosis or prosthesis exists.

SUMMARY

In accordance with an aspect of the present invention there is provided a variable gain impedance controller for use in a control system for controlling a prosthetic or orthotic apparatus provided with a joint, the controller comprising:

a sensor input for receiving a signal indicative of an interaction between the apparatus and the ground;

a torque sensor input for receiving a signal indicative of the torque at the joint; and a variable gain scheduler in communication with the sensor input so as to receive data therefrom thereby providing a variable torque gain;

wherein the variable gain impedance controller adjusts its control on the apparatus based on the variable torque gain and the indicated torque so as to increase the joint resistance to motion when the signal received from the sensor input indicates an interaction between the apparatus and the ground.

In accordance with another aspect of the present invention there is provided a variable gain impedance controller for use in a control system for controlling a motorized prosthetic or orthotic apparatus provided with a joint, the controller comprising:

a sensor input for receiving a signal indicative of an Interaction between the apparatus and the ground;

a torque sensor input for receiving a signal indicative of the torque at the joint; and a variable gain scheduler in communication with the sensor input so as to receive data therefrom thereby providing a variable torque gain;

wherein the variable gain impedance controller adjusts its control on the apparatus based on the variable torque gain and the indicated torque so as to decrease the joint resistance to motion when the signal received from the sensor input indicates an absence of interaction between the apparatus and the ground.

In accordance with a further aspect of the present invention there is provided a variable gain impedance controller for use in a control system for controlling a motorized prosthetic or orthotic apparatus provided with a joint, the controller comprising:

a sensor input for receiving a signal indicative of an interaction between the apparatus and the ground;

a torque sensor input for receiving a signal indicative of the torque at the joint; and a variable gain scheduler in communication with the sensor input so as to receive data therefrom thereby providing a variable torque gain;

wherein the variable gain impedance controller adjusts its control on the apparatus based on the variable torque gain and the indicated torque so as to a) increase the joint resistance to motion when the signal received from the sensor input indicates an interaction between the apparatus and the ground, and b) decrease the joint resistance to motion when the signal received from the sensor input indicates an absence of interaction between the apparatus and the ground.

BRIEF DESCRIPTION OF THE FIGURES

Embodiments of the invention will be described by way of example only with reference to the accompanying drawings, in which.

DETAILED DESCRIPTION

Generally stated, the non-limitative illustrative embodiment of the present invention provides a reactive layer control system for motorized prosthetic or orthotic devices for restoring lost locomotor functions, or facilitate gait re-education resulting from various pathologies occurrence. The reactive layer control system is part of a multi-layered controller and is based on impedance control, which directly manages a subset of lower-limb joint behaviors allowing the sustaining of highly efficient mechanical power exchanges between the user and a prosthetic or orthotic apparatus.

Figure 1:
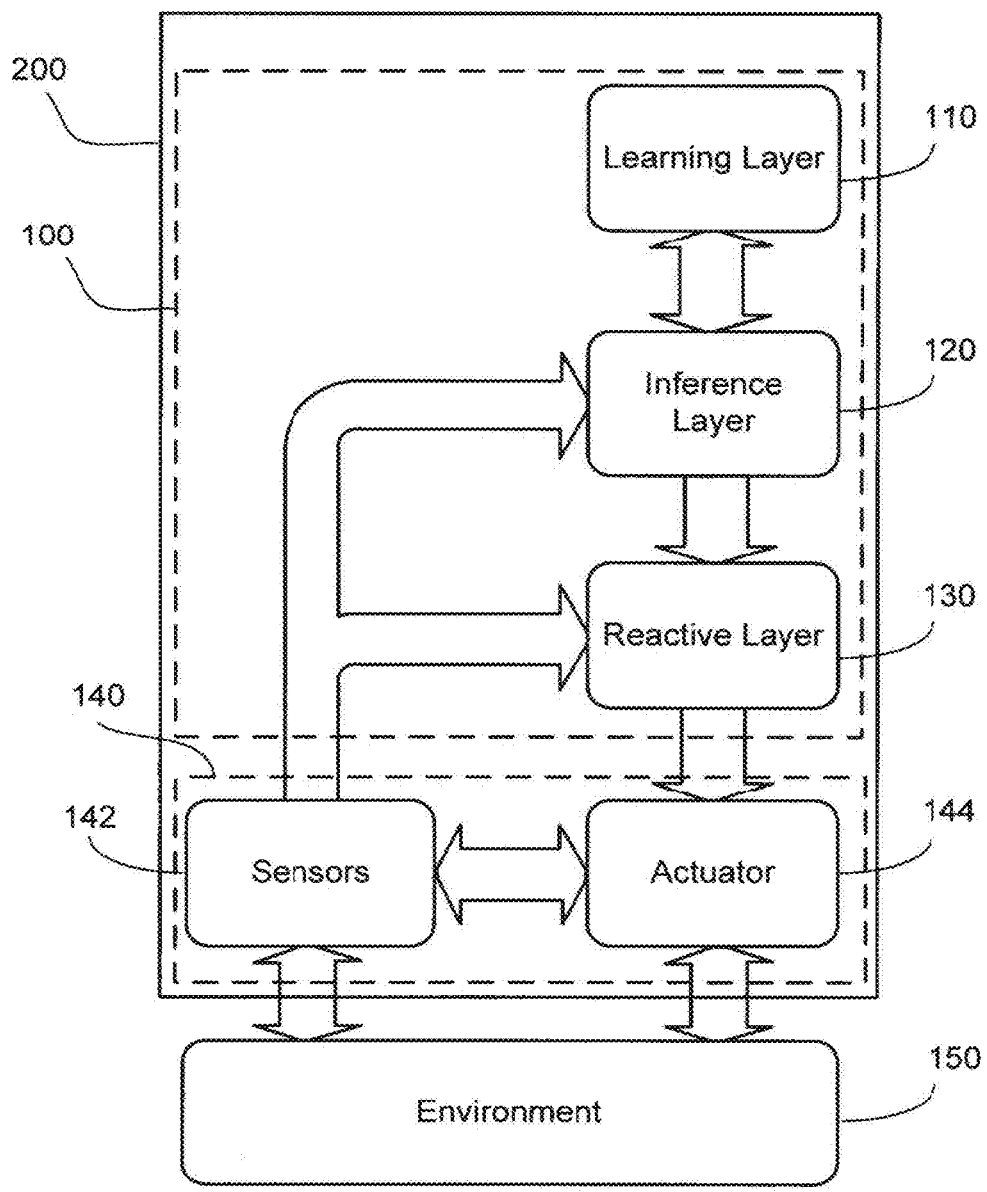
FIG. 1 is a block diagram of the interaction between various control system layers and major building blocks of a motorized prosthetic and/or orthotic device.
Figure 2:
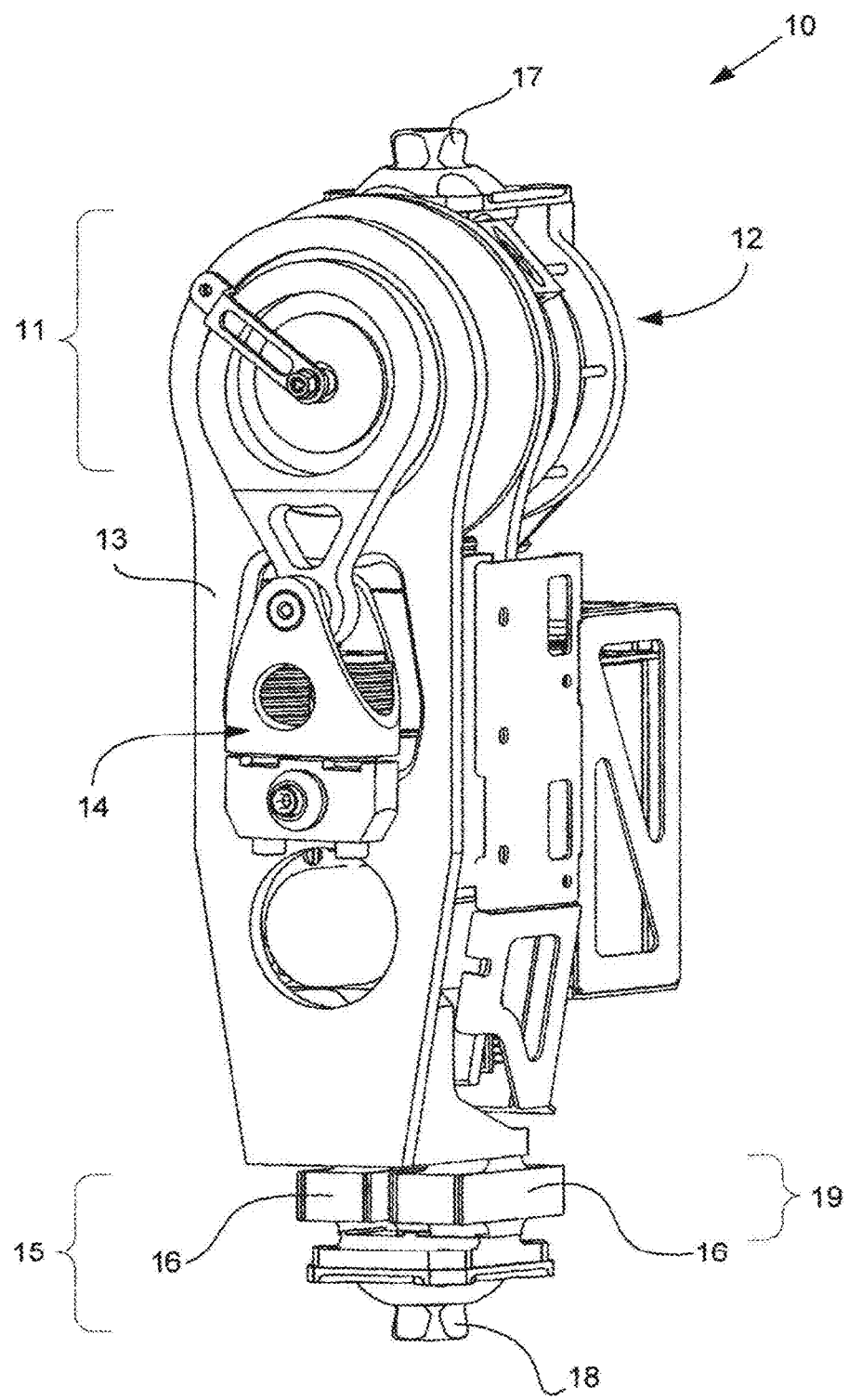
FIG. 2 is an isometric view of a motorized knee prosthesis.

Referring to FIG. 1, there is shown a block diagram of a motorized prosthetic and/or orthotic device 200 which comprises a multi-layered controller 100 that may be used to control a motorized prosthetic or orthotic apparatus 140 such as, for example, the motorized knee prosthesis 10 of FIG. 2.

Referring now to FIG. 2, the motorized knee prosthesis 10 includes a proximal connector 17 sitting on top of an actuator 12 which is axially mounted at the knee joint 11 level. In this example, the actuator 12 may be, for example, a DC brushless motor serially connected to a reduction mechanism. The reduction mechanism of the actuator 12 allows the conversion of the motor high-speed low-torque output characteristics into a low-speed high-torque output that is more coherent with the requirements associated with the human knee joint role in most commonly encountered locomotor tasks. A second transmission stage is then provided in order to connect the reduction mechanism output to the shank structure 13 of the motorized knee prosthesis 10. This second transmission stage is composed of a compliant linkage 14, allowing both measurement of the net torque present at the interface between the shank structure 13 and the actuator 12 output and high-efficiency level walking stance flexion energy storage and return.

The motorized knee prosthesis 10 also integrates sensors required to sustain the multi-layered controller 100 (see FIG. 1). A first position encoder (not shown) is integrated to the transmission assembly of the actuator 12 such that the relative position between the user thigh segment (not shown) and the reduction mechanism output is measured in real-time. Net torque present at the interface between the shank structure 13 and the actuator 12 output is measured through the deflection of the compliant linkage 14 transmitting motion between both parts 12, 13, using a second position encoder (not shown) mounted in the transmission assembly of the actuator 12 for that purpose. A load cell assembly 19 containing one or two load cells 16 is located at the distal shank portion 15, between the shank structure 13 and the distal connector 18 of the motorized knee prosthesis 10, to quantify the stress found in the distal shank portion 15.

It is to be understood that although the motorized knee prosthesis 10 described above has been given as an example of the motorized prosthetic or orthotic apparatus 140, the multi-layered controller 100 may be similarly used with other motorized prostheses or orthoses having general characteristics similar to that of the motorized knee prosthesis 10. More specifically, the multi-layered controller 100 may be similarly used with motorized or actuated prostheses or orthoses having means for measuring the net torque of its actuator output, means for detecting ground contact and means for measuring the position of its actuator.

Referring back to FIG. 1, the multi-layered controller 100 is particularly well suited for optimizing the synergy between a user and motorized prosthetic and/or orthotic device 200 through the implementation of motorized prosthetic or orthotic apparatus 140 joint behaviors similar to those which may be observed on a sound human knee joint.

The multi-layered controller 100 includes, but is not limited to, three layers herein referred to as the learning layer 110, the inference layer 120 and the reactive layer 130. Layering of the multi-layered controller 100 aims at providing a systematic way of distributing the functionalities of the multi-layered controller 100 with respect to their level of abstraction, hence allowing the definition of a coherent and straightforward architecture. It is to be understood that the multi-layered controller 100 may include more or less than three layers.

In order to interact with the environment 150 it evolves in, the motorized prosthetic and/or orthotic device 200 includes, but is not limited to, sensors 142 providing information about the environment 150 and the motorized prosthetic or orthotic apparatus 140 to the multi-layered controller 100, and one or more actuator 144, controlled by the multi-layered controller 100, to generate behavior allowing to sustain an optimal interaction with the environment 150. For example, in the case of the motorized knee prosthesis 10 of FIG. 2, the first and second position encoders (not shown), the compliant linkage 14 and the load cells 16 would compose sensors 142 while the actuator 12 would compose actuator 144.

Multi-Layered Controller

While all three layers 110, 120, 130 of the multi-layered controller 100 operate as stand-alone entities, information is propagated across the layers 110, 120, 130 such that lower-level layer mechanisms may beneficiate from information provided by higher-level layers. In such a multi-layered controller 100, decisions are performed independently inside of the different layers 110, 120, 130 characterized by different data abstraction levels, while propagation of information towards the lower-level layers ensures the adaptation of the lower-level layer mechanisms. In a similar fashion, information provided by the lower-level layers is merged into higher abstraction level representations when moved towards the higher-level layers.

Learning Layer

The learning layer 110 represents the highest data abstraction level of the multi-layered controller 100. More specifically, the data abstraction level associated with this layer is characterized as the user data. Functionalities associated with this level of the multi-layered controller 100 relate to the recursive improvement of the high level strategies to address locomotion tasks, as they are accomplished, and their relative performance assessed. At this level, representations of the user gait specificities identified during the evolution of the synergy between the user and the motorized prosthetic and/or orthotic device 200 are updated and stored.

Inference Layer

The inference layer 120 contains locomotion task level information and functionalities. At this abstraction level are found the engines required to perform locomotion task identification and characterization. Most of the work performed at this level consists in extracting typical features from the raw input data stream from the sensors 142 such that the locomotion task performed by the user may be characterized and system behavior adjusted according to the high-level information readily available from the learning layer 110.

Reactive Layer

At the lowest level, the reactive layer 130 sustains the implementation of general classes of joint behaviors that are common to a large subset of locomotor and non-locomotor activities. Similarly to the arc-reflex present in the human locomotor system, the reactive layer 130 is used in order to directly link low-level sensory inputs from the sensors 142 to either joint actions or behaviors of motorized prosthetic or orthotic apparatus 140 through the actuator(s) 144. Major benefits associated with integration of such reactive behaviors in a multi-layered controller 100 arise from the fact that these behaviors allow a reduced dependency on high-level decisions in order to implement specific actions.

Reducing dependency between high-level decision making and actions allows the reduction of latencies related to processing of high-level information and to generate simpler, more robust, mapping between sensory inputs from the sensors 142 and actions via the actuator(s) 144. Moreover, while generating more human-like behaviors from a user perspective, such implementation provides greater flexibility to the user who now find himself in full control of the motorized prosthetic or orthotic device's 200 most basic behaviors.

Linking low-level triggering mechanisms to the basic joint behaviors increases system conviviality and realm of performance, as it is still possible to trigger higher-level mechanisms generating more complex joint behaviors or motions, that will be simply defined as specialization of the more basic behaviors. This way, complex motions or elaborate joint behaviors may be generated from adding specific information to the basic behavior implicitly provided by the lowest-level layers of the multi-layered controller 100.

An example of a controller implementing a learning layer 110 and an inference layer 120 is shown in US Patent Application Publication No. 2006/0122710 A1 entitled "CONTROL DEVICE AND SYSTEM FOR CONTROLLING AN ACTUATED PROSTHESIS" by Bedard. The reactive layer 130 will be further explained below.

Reactive Layer Control System

A reactive layer control system for motorized prosthetic or orthotic devices according to an illustrative embodiment of the present invention relates to the definition of a reactive layer engine which may be used within the context of a multi-layered controller, such as the multi-layered controller 100 of FIG. 1.

The reactive layer control system is based on a variable gain impedance controller and has for goal to increase the synergy between the user and the motorized prosthetic and/or orthotic device 200 for all types of locomotion activities while directing specific attention towards system performance improvement for non-cyclical ambulation tasks. Improvement of motorized prosthetic and/or orthotic device 200 performance for limited ambulation locomotion tasks requires a greater flexibility of the reactive layer 130 such that general motorized prosthetic and/or orthotic device 200 behaviors may fulfill user requirements in a non-model based framework. Use of a model-based framework to manage locomotion tasks not presenting obvious physiological characteristics or high inter-subject variability presents severe limitation to the motorized prosthetic and/or orthotic device 200. Failure to generate a complete and robust mapping between the sensory inputs and the required actions actually impairs the general feasibility of a model-based framework.

However, definition of basic motorized prosthetic or orthotic apparatus 140 joint behaviors showing high correlation to the lower-limb joints physiological behavior and their integration to the lowest level of a multi-layered controller, such as the multi-layered controller 100 of FIG. 1, allows to implicitly fulfill specific tasks requirements, while leaving full control of the motorized prosthetic and/or orthotic device 200 behavior to the user.

The overall objective of the reactive layer control system is to reduce the dependency between decision and action for a general class of behaviors that may be compared to human arc-reflex. The general class of behaviors is found as the basic behaviors underlying most of the locomotion tasks. Implementation of reactive behaviors in the motorized prosthetic and/or orthotic device 200 leads to an increase in robustness and a significant reduction of the constraints associated with traditional decision process for a system where all actions are sustained by explicit decisions.

High fidelity reproduction of the human knee joint natural behavior is required in order to properly sustain limited ambulation tasks, generally improve mechanical power exchange management and ease constraints related to synchronization of the motorized prosthetic or orthotic apparatus 140 joint behavior transition with overall dynamics of the user.

Human knee joint role in gait for locomotor and non-locomotor tasks may be classified in general classes of joint behaviors as illustrated in the following table:

TABLE 1

Joint behavior classes

| Joint behavior class | Behavior | Reactive Controller Behavior |
|---|---|---|
| Passive | motion without force (e.g., aerial phase) | perturbation force matching |
| Isometric | support without motion (e.g., contact phase) | perturbation force rejection |
| Eccentric | energy dissipation | braking |
| Concentric | mechanical power generation | energy injection |

These general classes of joint behavior may then be directly managed through the implementation of an associated reactive layer controller behavior.

Impedance Control

The reactive layer control system is built around a typical implementation of an impedance controller. The impedance controller was first introduced by Hogan in 1985, see [1], [2] and [3], as a first step in defining a general and unified approach to the control of manipulation by robotic devices. While being very general, this specific control scheme is rather well suited for managing tasks where highly dynamic interactions between a robotic device and the environment are present. Apart from other traditional control schemes targeting the individual control of actuator variables such as torque or position control, impedance control implements a scheme where the overall objective is defined as implementing a dynamic relationship between actuator variables, such as torque and position. In other words, the impedance controller does not try to track specific trajectories, but instead attempts to regulate the relationship between actuator velocity and force. The dynamic relationship between actuator force and velocity is generally known as "mechanical impedance". This nomenclature arise from similarity to the electrical quantity found as the ratio of an effort variable (i.e. voltage) to a flow variable (i.e. current). In the Laplace domain, mechanical impedance may be represented as follows:

$$Z(s) = \frac{F(s)}{V(s)} \qquad \text{Equation 1}$$

where
  Z(s) is the mechanical impedance;
  F(s) is the actuator force; and
  V(s) is the actuator velocity.

At the opposite, mechanical admittance describes the dynamic relationship between actuator velocity and force. In the Laplace domain, mechanical admittance may be represented as follows:

$$Y(s) = \frac{V(s)}{F(s)} \qquad \text{Equation 2}$$

where
  Y(s) is the mechanical admittance;
  V(s) is the actuator velocity; and
  F(s) is the actuator force.

While the relationships represented by Equations 1 and 2 are generally interchangeable for linear systems operating at finite frequencies, this is not the case for typical prosthetic or orthotic applications, which are generally highly non-linear. Moreover, due to the input-output specificities of the mechanical system behaviors described above, it is only possible to physically connect components of different nature. Failure to fulfill this requirement actually makes impossible proper management of the mechanical power exchanges at the interface ports, as both components will try to impose the same physical quantity.

Figure 3:
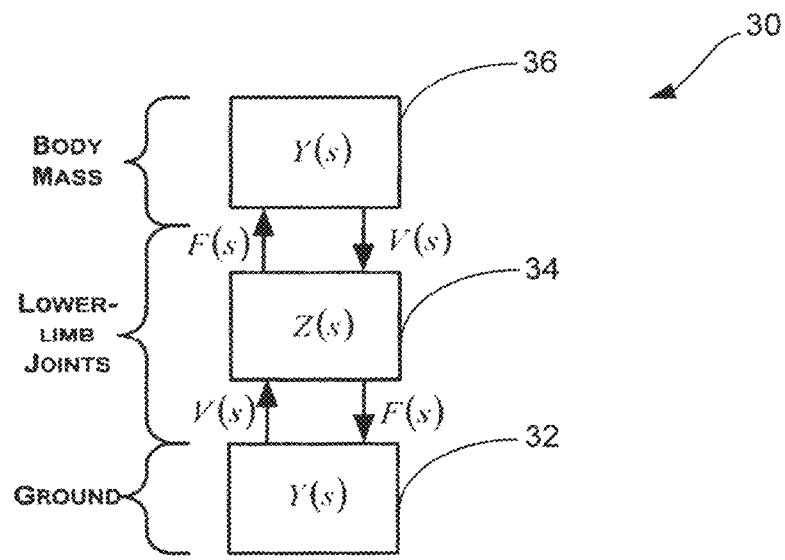
FIG. 3 is a schematic representation of the lower-limb mechanical power exchange during ground contact phase.
Figure 4:
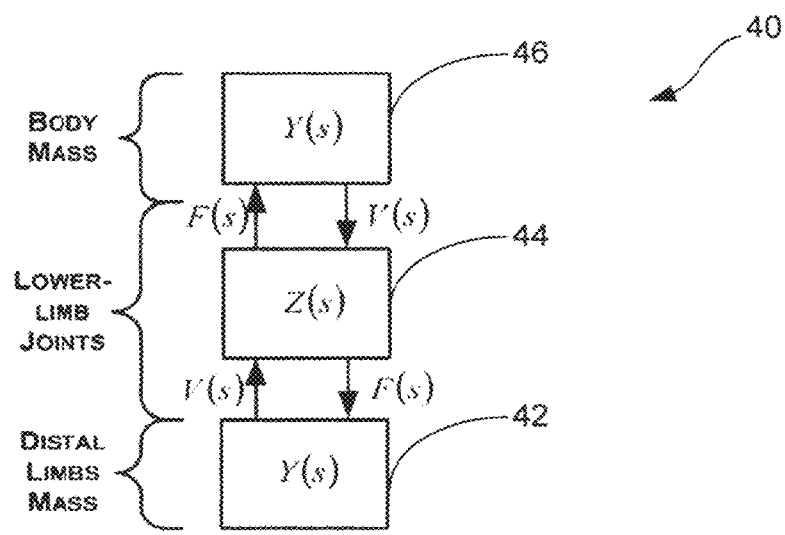
FIG. 4 is a schematic representation of the lower-limb mechanical power exchange during aerial phase.

As far as the description of lower-limb joints physical behavior is concerned, one has first to consider that the structure of the human lower-limb, coupled with locomotor and non-locomotor gait specificities, generate two different mechanical configurations 30, 40, represented conceptually in FIGS. 3 and 4, respectively. In a first configuration 30, the lower-limb joint 34 is located between the external environment (i.e. ground) 32 and the user's upper body mass 36. In a second configuration 40, the lower-limb joint 44 is located between the hanging distal limb mass 42 and the user's upper body mass 46, and is thus submitted to significant dynamic efforts. For the first configuration 30, velocity constraints are imposed on the lower-limb joints 34 (i.e. healthy joints and prosthetic or orthotic joints) by the ground 32 on the distal end and by the user's upper body mass 36 on the proximal end. As for the second configuration 40, velocity constraints are imposed on the lower-limb joints 44 (i.e. healthy joints and prosthetic or orthotic joints) by the distal limb 42 (residual limb or prosthesis) dynamics on the distal end and by the user's upper body mass 46 on the proximal end.

It is to be understood that "ground" is meant to mean, in the context of this specification, any surface on which a user may use the motorized prosthetic and/or orthotic device 200 during locomotion activities Ground Contact Phase FIG. 3 provides a high-level representation of the lower-limb components interactions during ground contact phase through the use of mechanical impedance/admittance. An impedance is a system characterized by its capacity to accept a flow input V(s) (i.e., velocity) and yield an effort F(s) (i.e., force). An admittance is a system characterized by its capacity to accept effort inputs F(s) (i.e., force) and yield a flow V(s) (i.e., velocity).

In order for mechanical power exchange to take place between both types of system, input-output variables V(s) and F(s) must be matched. Since it is not possible to impose a velocity to the ground 32, it is modeled as an admittance. Connecting any type of lower-limb device to the ground 32 then requires this latter to be defined as an impedance. Furthermore, the upper body mass 36 is also modeled as a admittance as it may only impose velocity on the lower-limb joints 34 and segments. Force observed in the lower-limb joints 34 during the ground contact phase then arise from the impedance of the joints themselves. Thus, it may be observed that in configuration 30, the lower-limb joints 34 form a system optimally represented as an impedance interacting with the user's body mass 36 and ground 32, both modeled as admittance.

Aerial Phase

FIG. 4 provides a high-level representation of the lower-limb components interactions during the aerial phase. In this configuration 40, the lower-limb joints 44 are mainly submitted to the effects of the distal limbs mass 42 and upper body mass 46. Again, a mass being characterized as an element that accepts force F(s) as input while yielding velocity V(s) as output, it appears necessary to define the behavior of the lower-limb joints 44 as an impedance in order to ensure that stable mechanical power exchanges may take place. Based on these observations, it appears clear that the definition of any lower-limb prosthetic or orthotic devices, motorized or not, must take the form of an impedance if it is desired to optimize user-device synergy and properly manage mechanical power exchange.

Furthermore, this is also coherent with the role of the lower-limb joints in cyclical locomotion activities, which consists in absorbing shocks generated by the ground contact occurrence, such that body centre of mass trajectory is regulated and smooth progression occurs. Use of an impedance controller in order to manage the prosthetic or orthotic joint behavior then appears as a straightforward solution to the problem at hand.

Impedance Controller

As previously introduced, the impedance controller differs from more traditional motion control schemes through the fact that it does not attempt to track specific control variables, such as force or position, but implements a scheme that allows regulation of the actuator 144 (see FIG. 1) output mechanical impedance. Furthermore, this specific scheme implicitly manages transitions where the actuator 144 physical configuration is changing from non-interacting configuration 40 with the environment to an interacting configuration 30 (see FIGS. 3 and 4), which is not the case with other types of control schemes.

Figure 5:
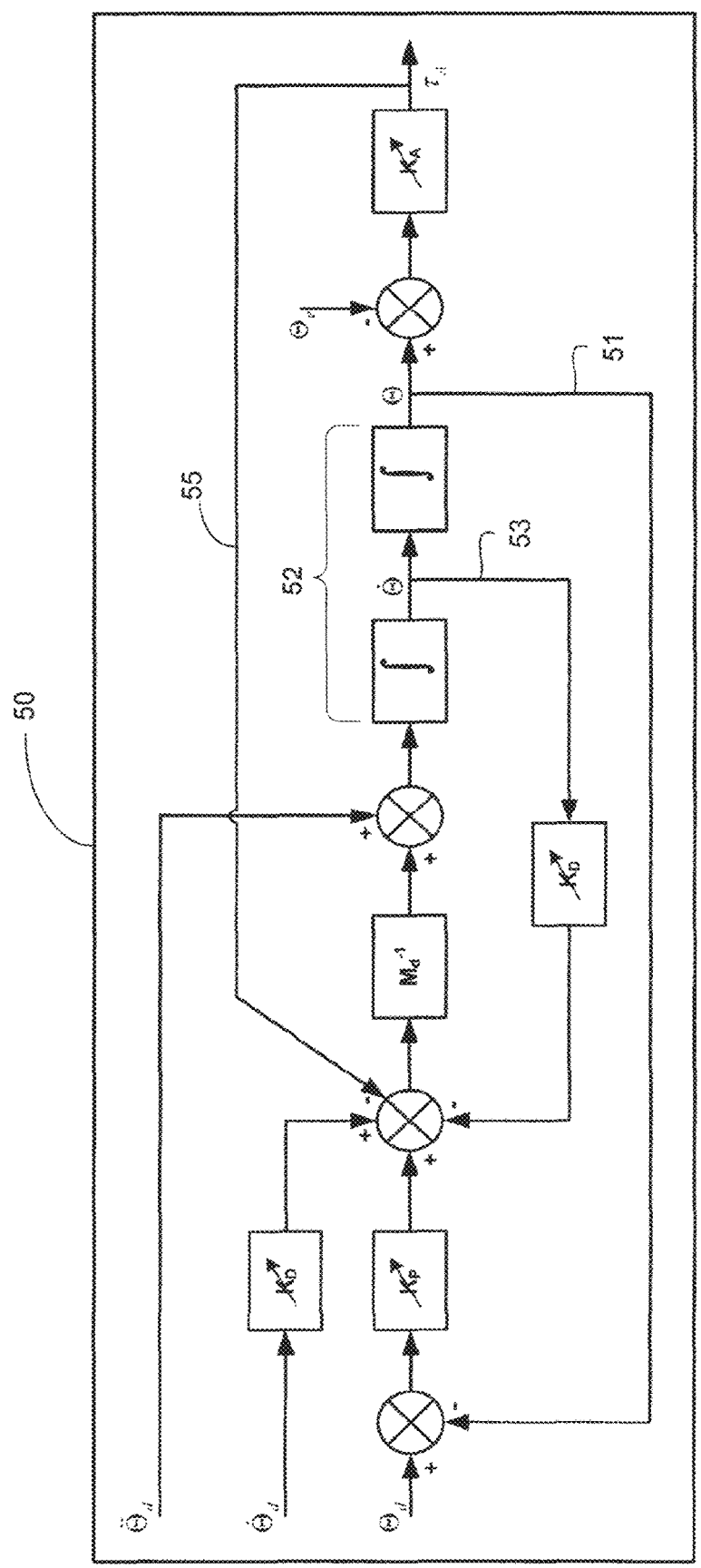
FIG. 5 is a block diagram of a variable gains impedance controller basic formulation.

Referring to FIG. 5, there is shown a basic formulation of a variable gains impedance controller 50 that may be implemented at the reactive layer 130 (see FIG. 1). The motorized prosthetic or orthotic apparatus 140 under control is represented by a Laplace-domain double integrator 52. First, position $\Theta$ and velocity $\dot{\Theta}$ feedback loops 51, 53 are closed to form a tracking controller where position $\Theta_d$ and velocity $\dot{\Theta}_d$ set-points are used as comparison values for the feedback position $\Theta$ and velocity $\dot{\Theta}$ values. Furthermore, variable gains $K_P$ and $K_D$ are applied to both position and velocity error terms (i.e., difference between the set-point values $\Theta_d$ and $\dot{\Theta}_d$, and the measured feedback values $\Theta$ and $\dot{\Theta}$). $\ddot{\Theta}_d$ represents the acceleration set-point.

Additionally to what would otherwise be considered as a simple proportional-derivative position controller, interaction between the actuator 144 output port position $\Theta$, with the position perturbation created by the environment $\Theta_e$, generates a generalized force $\tau_A$ quantifying the interaction force between the actuator 144 output and its environment. This measured force value $\tau_A$ is then used as a negative feedback loop 55, creating an actuator 144 set-point value of the same amplitude as the interaction force, assuming unitary force feedback gain $K_A$, but of opposite sign. Assuming that satisfactory force sensing capacities are available, such system would then show an infinite impedance (i.e. any perturbation force applied on the actuator 144 output would be immediately converted to an opposite actuator 144 reaction, leading to no displacement of the actuator 144 under the action of the external force) without any contribution of the position $\Theta$ and velocity $\dot{\Theta}$ terms. Modification of the force feedback term gain $K_A$ allows the scaling down of the actuator 144 mechanical impedance by reducing the amount of force that is sent back as actuator 144 set-point.

In such a variable gains impedance controller 50, position $\Theta$ and velocity $\dot{\Theta}$ terms are used to generate the system dynamic response to either effects of external perturbation $\Theta_e$ or modifications to the system's position $\Theta_d$ and velocity $\dot{\Theta}_d$ set-points. Such combination of proportional-derivative position control and the measured interaction force allows the full compensation of any perturbation present at the system mechanical interaction port, while still allowing to enforce a specific dynamic response.

A final gain, the mass gain $M_d^{-1}$, affects the complete actuator 144 force set-point and is generally considered to allow simulation of system apparent inertia through appropriate scaling of the variable gains impedance controller 50 output. While the variable gains impedance controller 50 basic behavior described above already provides an interesting framework for managing interactions and mechanical power exchanges between the user and the motorized prosthetic and/or orthotic device 200, coupling of the variable gains impedance controller 50 with a gain scheduling mechanism, which will be described further below, is shown to further extend the realm of implicitly supported behaviors. While use of high-level engines to manage gain scheduling allows the adaptation of prosthetic or orthotic apparatus 140 joint behaviors based on the nature of the locomotion tasks currently executed, lower-level gain scheduling engines allow the adaptation of the variable impedance controller parameters such that optimal use of the inherent behaviors of the variable gains impedance controller is made without compromising system performance from an user standpoint.

The above described variable gains impedance controller 50 may be used to implicitly implement the first two joint behavior classes of Table 1, namely the Passive and Isometric classes, while its general structure may be used to explicitly integrate the third and fourth joint behavior classes, namely the Eccentric and Concentric classes.

Force Matching and Force Rejection Implementations

As discussed above, the first two joint behavior classes, i.e. Passive and Isometric, are addressed through proper usage of the implicit behaviors of the variable gains impedance controller 50. These first two joint behaviors classes are considered the most basic ones as all locomotion task will first be characterized as being composed of one, or both, of these behaviors.

The behavior of the Isometric joint behavior class corresponds to a joint behavior where force without motion is generated, and will be herein associated to a joint behavior where it is desired to provide stability and support, without generating any motion. This behavior is associated with the stance phase of all cyclical and non-cyclical locomotion tasks, where it is advantageous from a safety and usability standpoint to be able to provide support to the user without enforcing any motion.

Referring back to FIG. 5, from a variable gains impedance controller 50 standpoint, such behavior corresponds to an infinite impedance of the actuator 144 output with respect to the effects of external perturbations $\Theta_e$. As previously introduced, such behavior is implicitly generated by the variable gains impedance controller 50 assuming that the force feedback gain $K_A$ is adequately selected. In order for an infinite impedance behavior to take place, magnitude of the measured interaction force must be very similar to the one of the force actually imposed on the actuator 144 output, force losses in the actuator 144 and transmission must be accounted for and latency of the actuator 144 reaction with respect to the external perturbation $\Theta_e$ must be small enough not affect the closed-loop stability of the variable gains impedance controller 50.

With reference to the motorized knee prosthesis 10 of FIG. 2, the variable gains impedance controller 50 force feedback loop 55 value $\tau_A$ may be provided by the measurement of the net torque found at the interface between the actuator 12 output and shank structure 13. As previously introduced, measurement of the deflection of the compliant element 14 provides a direct measure of the net torque. While measuring the net torque through a compliant element 14 greatly reduces the sensing bandwidth with respect to other technologies, such technique is shown to provide satisfactory results in the context where human motions are showing only limited bandwidth and allow some flexibility with respect to system reaction latency.

From a usability perspective, it is advantageous for the motorized prosthetic and/or orthotic device 200 (see FIG. 1) to provide support to the user without actually impairing his capacity to voluntarily move the system 200 from a given position to another one, while maintaining prosthetic or orthotic apparatus 140 joint stability. Such setting is found through the adequate adjustment of the force feedback gain $K_A$ until satisfactory joint impedance is obtained, i.e. leading to a non-infinite joint impedance, with respect to user ability level and personal preferences.

In a similar manner, the passive joint behavior may be directly implemented using the inherent characteristics of the variable gains impedance controller 50. As the Passive joint behavior class is directly associated with the aerial phase of any locomotion task, it is advantageous to make the motorized prosthetic and/or orthotic device 200 as compliant as possible, such that overall user-device synergy may benefit from the direct interactions between user residual limb motions and the inertial properties of the motorized prosthetic or orthotic device 200. Moreover, making the motorized prosthetic and/or orthotic device 200 as compliant as possible during the aerial phase allows the minimization of the inertia reflected at the stump-socket interface (for example, the socket, which is not shown, connects to the proximal connector 17 of the motorized knee prosthesis 10 of FIG. 2). This way, a significant reduction of the apparent weight of the motorized prosthetic and/or orthotic device 200 is obtained from a user perspective, while the motorized prosthetic and/or orthotic device 200 also becomes easier to manipulate.

From a variable gains impedance controller 50 standpoint, generating a minimum impedance behavior during the aerial phase requires the actuator 144 command signal to act in such a way that the force measured at the actuator 144 output remains null or negligible. Obviously, this requires the actuator 144 output to move in the same direction as the shank structure 13, such that the net force between both parties remains null or negligible. Assuming again a null contribution of the proportional and derivative terms of the variable gains impedance controller 50, i.e., $K_P \cong 0$ and $K_D \cong 0$, this behavior is achieved by modifying the force feedback gain $K_A$ value such that the measured interaction force now becomes a positive set-point to the actuator 144, i.e., achieved by inverting the sign of the force feedback gain $K_A$.

Assuming proper selection of the force feedback gain $K_A$ value and minimal latency of the actuator 144 command with respect to the measured force, minimal joint impedance is obtained. Such scheme also provides the benefit of compensating for the actuator 144 mechanical non-linearities, which are known to greatly affect the passive dynamic properties of motorized prosthetic or orthotic systems. This is the major difference between using null gains in a position control scheme and performing perturbation force matching with the variable gains impedance controller 50. While the position control system would simply turn off the actuator 144, the variable gains impedance controller 50 with the perturbation force matching approach allows to compensate for actuator 144 dynamic non-linearities, i.e. transmission back-driving torque, actuator motor cogging, actuator motor and transmission bearings friction, hence really minimizing joint impedance. In fact, in the motorized knee prosthesis 10 of FIG. 2, only the friction found in the shank structure 13 bearings is not compensated through the perturbation force matching scheme.

Full compensation of the actuator 144 dynamic non-linearities would require measurement of the external perturbation $\Theta_e$ force at another level of the structure, for example at the foot-ground interface. Nevertheless, measurement of the external perturbation $\Theta_e$ force at the actuator 144 output is found more flexible with respect to lower-limb mechanical configuration and ensure high co-linearity between force measurement and actuator 144 output.

As introduced earlier, modification of the gains of the variable gains impedance controller 50 is required in order to change the joint behavior of the motorized prosthetic or orthotic apparatus 140 from a finite impedance level to a null impedance level. This change is limited in scope and is directly correlated with the lower-limb mechanical configurations 30, 40, represented conceptually in FIGS. 3 and 4, i.e., ground contact and aerial phase respectively. In order for the reactive layer 130 behavior to take place without affecting overall motorized prosthetic and/or orthotic device 200 performance, it is advantageous to minimize decisional overhead and device behavior transition latency from a user perspective.

Gain Scheduling Mechanism

Figure 6:
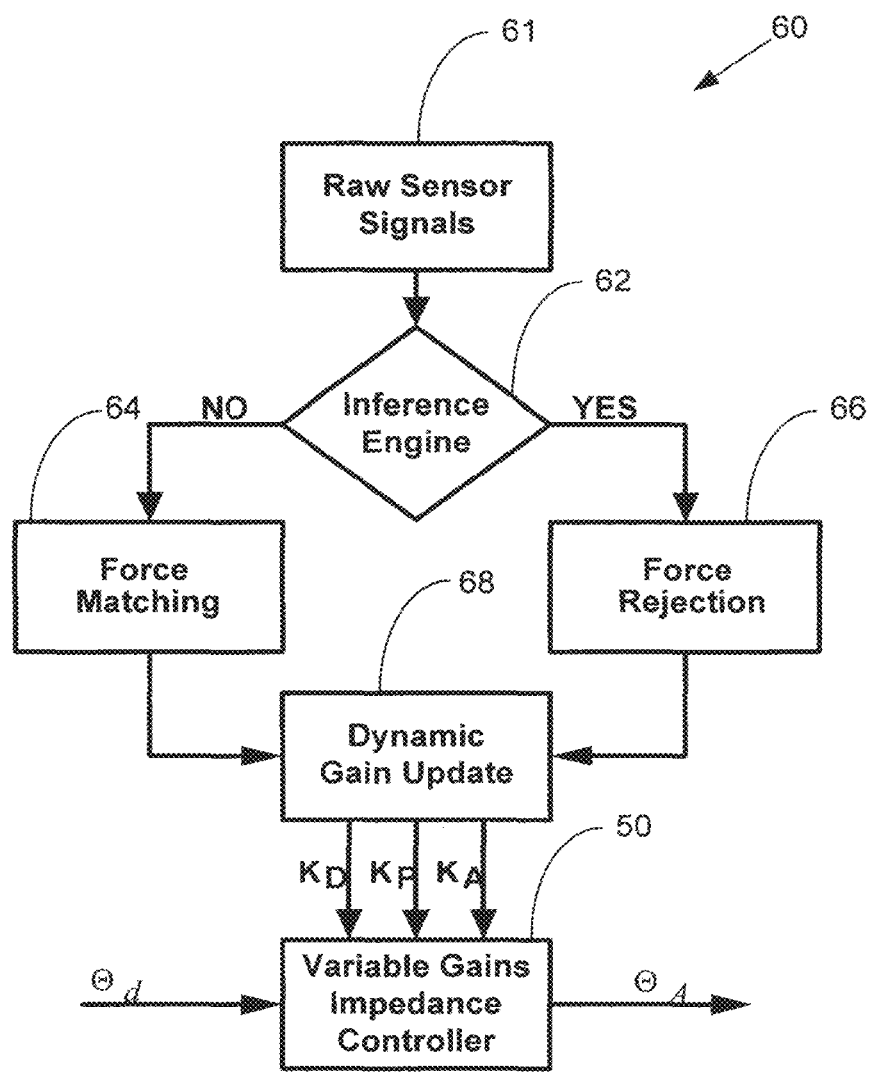
FIG. 6 is a flow diagram of a gain scheduling mechanism and associated reference engine.

Referring to FIG. 6, there is shown a simplified block diagram of a low-level gain scheduling mechanism and associated inference engine 60 that may be used in order to modify the behavior of the motorized prosthetic and/or orthotic device 200 where a transition from the lower-limb interacting mechanical configuration 30 to the non-interacting configuration 40, or the opposite, is detected. First, raw sensor signals 61 from the sensors 142 (see FIG. 1) are provided to a detection mechanism in the form of an inference engine 62 in order to identify if the lower-limb mechanical configuration is interacting 30 or non-interacting 40 (see FIGS. 3 and 4) by, for example, detecting ground contact. Various types of sensors 142 may be used in order to sustain the decisional process of the inference engine 62, for example instrumented plantar orthosis, accelerometers, digital switches, load cells, etc. Advantageously, with reference to FIG. 2, a load cell assembly 19 containing one or two load cells 16 located at the distal shank portion 15 maybe used to provide the raw sensor signals 61.

The decisional process of the inference engine 62 may implement low-pass filtering of the raw sensor signals 61 combined with single value hysteretic thresholding of the low-pass filtered raw sensor signals 61 in order to identify the lower-limb mechanical configuration 30, 40. Based on the result of the thresholding process, a perturbation force matching 64 or perturbation force rejection 66 gain scheme is provided to the dynamic gain update process 68.

The dynamic gain update process 68 then proceeds to the dynamic update of the gains of the variable gains impedance controller 50 using, for example, linear transition patterns or other patterns, where the transition duration is configurable in order to adapt to user personal preferences and gait specificities. In the illustrative embodiment, only the proportional $K_P$, derivative $K_D$, and force feedback $K_A$ gains are modified. The mass gain $M_d^{-1}$ is maintained unitary and constant. Moreover, while the force feedback gain $K_A$ transition from a negative value to a positive value upon occurrence of a ground contact event, the proportional $K_P$ and derivative $K_D$ gains are maintained to the same values, which are voluntarily selected close to zero. Based on results from experimental trials, a substantially unitary positive force feedback gain $K_A$ during the ground phase coupled to a substantially unitary negative feedback gain $K_A$ during the aerial phase leads to an optimal gain configuration.

Reactive implementation of the Passive and Isometric joint behavior classes by the variable gains impedance controller 50 provides the underlying foundations to the implementation of any locomotion task and will also define the default behavior of the motorized prosthetic and/or orthotic device 200. Based on the fact that the combination of these behaviors will sustain all limited ambulation tasks, while leaving the user in full control of the management of mechanical power exchanges, benefits arising from such a scheme are multiple, namely:

- no requirement for a orthotic or prosthetic device-user synchronization mechanism as transitions are initiated by the user and the reaction time of the motorized prosthetic and/or orthotic device 200 is quite short;
- no requirement for high-level detection of transitions between isometric and passive joint behavior classes, reducing latencies caused by complex detection mechanisms and delay required to ensure stable transition of the behavior of the motorized prosthetic and/or orthotic device 200;
- motorized prosthetic and/or orthotic device 200 joints limited impedance in aerial phase increases ease of manipulation in confined spaces and when maneuvering around obstacles;
- cyclical locomotion tasks initiation is facilitated as the user provides himself the proper pace and stride length; and
- as the gait cycle patterns are not issued from a model, or trajectory generation engine, or time-based mechanism, any activity or gait phase may be interrupted at any instant without compromising user support and safety.

Braking Implementation

The third class of lower-limb joint behavior, the Eccentric class, may be advantageously addressed through a software-based braking mechanism implementation. The Eccentric class of joint behavior is concerned with the dissipation of energy by the joint of the motorized prosthetic or orthotic apparatus 140 (see FIG. 1). Generally speaking, the energy is injected from an external source and requires dissipation in order to properly manage joint behavior and resulting motion. For example, on the human healthy limb, Eccentric joint behavior is observed at each extremity of the level walking swing phase, where it is required to stop the knee joint motion due to shank inertia. Moreover, the use of the perturbation force matching behavior previously introduced in the aerial phase tends to accentuate this issue by giving a very low impedance to the knee joint.

While multiple approaches exist to solve this type of problem, it is advantageous to implement the Eccentric joint behavior class in a reactive fashion to ensure constant behavior and performance from the user standpoint. Moreover, it is advantageous to avoid the use of a trajectory-based mechanisms that only provide limited flexibility and require much tuning to account for inter-user variability.

Figure 7:
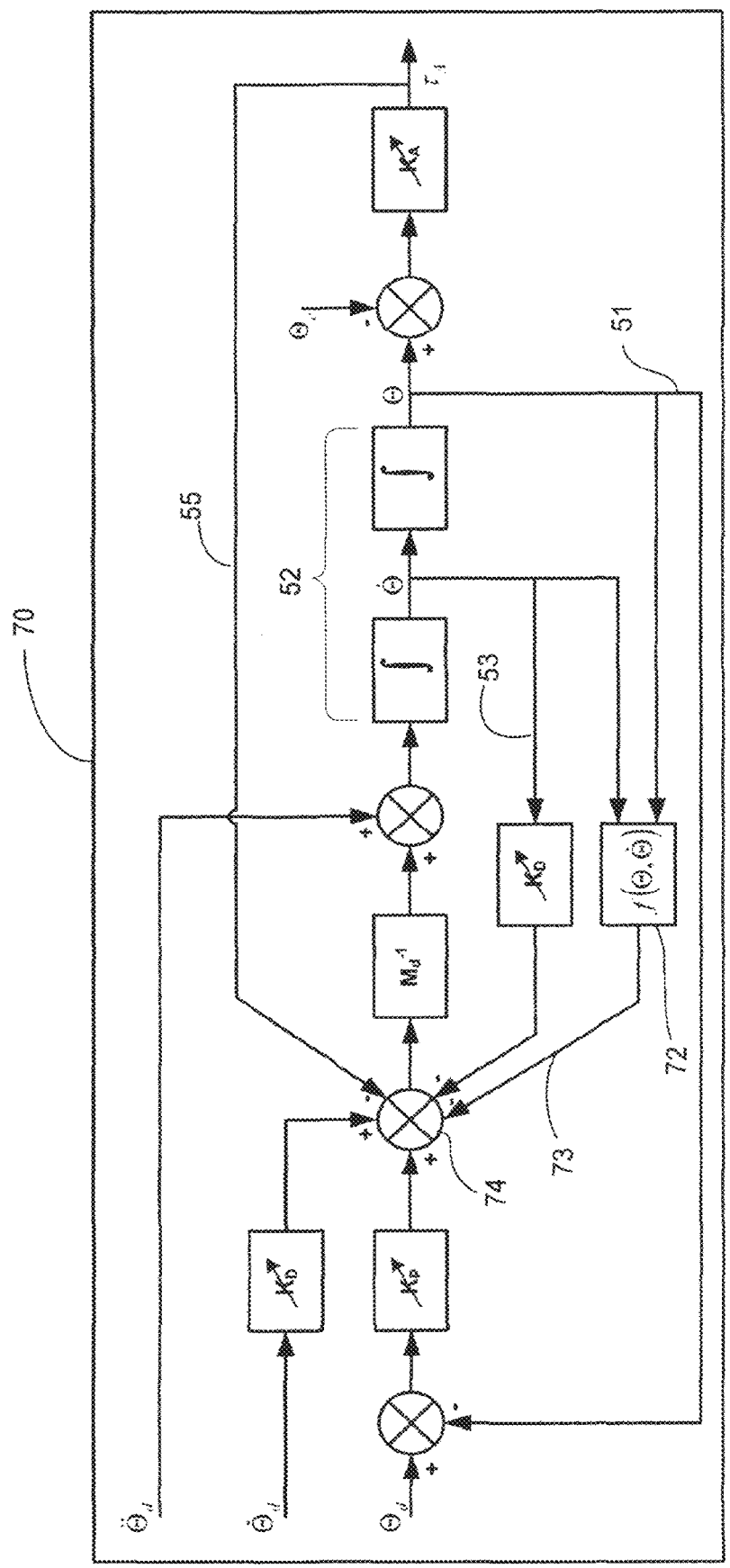
FIG. 7 is a block diagram of a variable gains impedance controller with breaking feedback transfer function.

Using the general framework provided by the variable gains impedance controller 50 shown in FIG. 5, explicit reactive behavior is added to the basic formulation, leading to the block diagram of FIG. 7. From a motorized prosthetic and/or orthotic device 200 perspective, implementation of the Eccentric joint behavior class for the aerial mechanical lower-limb configuration 40 (see FIG. 4) is equivalent to managing braking using the actuator 144. Actuator 144 braking in the aerial configuration 40 may be achieved using many approaches: reduction of the perturbation force matching 64 (see FIG. 6) effort in order to allow natural dissipation to take place, increase of the actuator 144 impedance, and reversal of the actuator 144 motion such that the motor torque is found in the opposite direction as its velocity.

FIG. 7 shows a variable gains impedance controller 70 based on the variable gains impedance controller 50 of FIG. 5 to which a braking process has been integrated, the braking process including all of the approaches described above. The braking joint behavior, associated with eccentric muscle activation on the sound limb, is active at all time but its action is controlled through a set of logical conditions on various system variables. Thus, the braking process may be integrated in the variable impedance controller 70 as a braking feedback transfer function 72 subject to conditional execution. Execution conditions are based on three main variables: actuator 144 output position $\Theta$, actuator 144 output velocity $\dot{\Theta}$ and lower-limb mechanical configuration 30, 40. While in the aerial configuration 40, the braking process is activated when a velocity threshold is reached in the vicinity of, for example, an end-of-motion bumper or a software-defined maximum target flexion angle.

Figure 8:
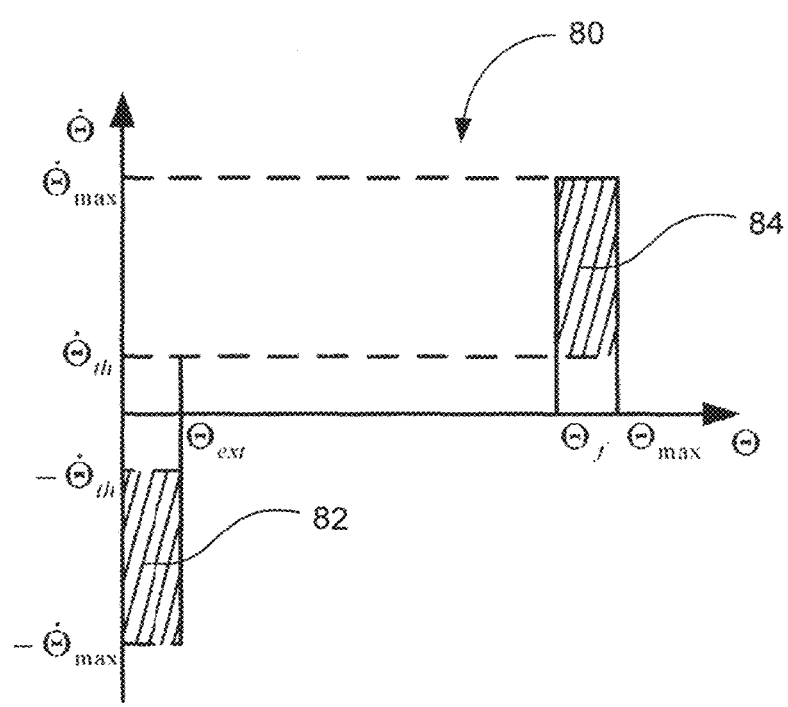
FIG. 8 is a chart illustrating the braking reactive behavior activation subspace.

FIG. 8 illustrates the velocity-position subspace 80 in which the braking process operates. The hatched regions 82, 84 represent the regions where the braking process is activated, otherwise, the braking process remains passive, i.e. $f(\Theta, \dot{\Theta})=0$. In the simplest embodiment of the braking process, the regions 82, 84 in which the braking process activates may be defined as both ends of the knee joint motion range of the motorized prosthetic or orthotic apparatus 140 (see FIG. 1). Whenever the joint enters one end of the motion range, delimited by the actuator 144 output angular position extension $\Theta_{ext}$ and output angular position flexion $\Theta_f$ activation thresholds, while showing velocity towards the nearest physical motion stop (i.e. bumper) superior to the output angular velocity activation threshold $\dot{\Theta}_{th}$, the braking process is activated in order to stop the joint and segment motion of the motorized prosthetic or orthotic apparatus 140 before reaching the physical motion stop. Upon activation of the braking process, the braking feedback transfer function 72 generates an output signal 73 that is removed from the net force command balance 74 that is used as the actuator 144 command signal.

More specifically, the braking feedback transfer function 72 may be defined as:

$$\text{if } (\dot{\Theta} < -\dot{\Theta}_{th}) \&\& (\Theta < \Theta_{ext}): \quad \text{Equation 3}$$
$$f = \frac{\dot{\Theta}}{(\Theta + \Delta)^2};$$
$$\text{if } (\dot{\Theta} > \dot{\Theta}_{th}) \&\& (\Theta > \Theta_f):$$
$$f = \frac{\dot{\Theta}}{(\Theta_{max} + \Delta - \Theta)^2};$$

otherwise:

f=0;

where
- f is the braking feedback transfer function;
- $\Delta$ is the position offset;
- $\Theta$ is the actuator output position measurement;
- $\Theta_{ext}$ is the actuator output position extension activation threshold;
- $\Theta_f$ is the actuator output position flexion activation threshold;
- $\Theta_{max}$ is the actuator output maximum achievable position;
- $\dot{\Theta}$ is the actuator output velocity measurement; and
- $\pm\dot{\Theta}_{th}$ is the actuator output angular velocity activation threshold.

Based on Equation 3, the braking feedback transfer function 72, or braking force, may then be defined as the ratio of the joint velocity $\dot{\Theta}$ to the squared position measurement $\Theta$, where an offset $\Delta$ is added to ensure that the braking force remains a finite quantity while reaching the motion range end. Using such a relationship to compute the braking force to be accounted in the net actuator 144 command calculation allows the creation of a braking force that increases as the joint move towards the motion end while maintaining a significant velocity, while not restricting motion in the direction opposite to the motion end. Such behavior differs from simply increasing the joint impedance of a motion tracking control scheme, as the behavior herein defined is characterized by its single sided action.

While Equation 3 is defined to ensure that braking occurs prior to reaching the hardware motion stops, it is also possible to dynamically configure the braking process parameters in order to modify the location in the motion range where braking occurs. Hence, this braking process may also be advantageously used in order to manage swing phase heel rise during cyclical portions, or for other specialized functions such as motion range limitations during rehabilitation or training processes. While the first suggested use could be fully automated through definition of the proper detection and adjustment mechanism in the inference layer 120 (see FIG. 1), the second suggested use would optimally be linked to a user/clinician interface device, allowing this interface device to configure the motorized prosthetic and/or orthotic device 200 according to the requirements of the rehabilitation/training process.

Referring back to FIG. 7, from a variable gains impedance controller 70 standpoint, the additional behavior is integrated as a supplementary feedback term 73 that is added to the basic formulation. Referring back to the motorized knee prosthesis 10 of FIG. 2, the braking feedback transfer function 72 uses as input the measured relative position between actuator 12 output and thigh segment (not shown), and the estimated joint velocity. Joint velocity may be estimated using an ARMA, i.e. Auto Regressive Moving Average process, which is shown to provide an estimate of sufficient quality while minimizing the requirement for hardware sensors. Upon fulfillment of the conditions illustrated in FIG. 8, the position measurement and velocity estimates are then used in order to compute the amplitude of the braking force.

As previously discussed, the braking force then acts on the variable gains impedance controller 70 behavior by reducing the force feedback sustaining the perturbation force matching process 64. Hence, the braking force first compensates for the force feedback term 55, leaving the actuator 144 in a passive mode. Leaving the actuator 144 in a passive mode when the joint is actually driven by inertial forces allows the use of the motorized prosthetic or orthotic apparatus 140 poor passive dynamics in order to fulfill the objective of the current joint reactive behavior, i.e. dissipation of energy in order to break joint motion. If the use of passive braking is not sufficient to stop the motion, the form of the braking transfer function 72 defined by Equation 3 generates a braking force that gains in amplitude as the joint continues to move towards the motion stop. As the braking force becomes greater than the perturbation matching force term, i.e. force feedback term 55, the actuator 144 starts generating a force in the direction opposed to the motion, which results in a quick stop of the motion. In the swing phase, i.e. the aerial phase 40, the actuator 144 behavior depends on the balance between the contribution of the force feedback term 55, and the proportional-derivative terms, i.e. $\Theta$ and $\dot{\Theta}$. Since $K_P$ and $K_D$ are set to 0 for the swing phase, actuator 144 behavior is then defined by the sum of the force feedback term 55 and the supplementary feedback term 73. Based on the definition of the breaking transfer function 72, the force feedback term 55 is first cancelled out by the supplementary feedback term 73 as the latter increases. As the supplementary feedback term 73 becomes larger than the force feedback term 55, the force following is effectively cancelled out and the supplementary feedback term 73 becomes the main contributor to the amplitude and direction of the command signal sent to the actuator 144. By their nature and definition, the force feedback term 55 and the supplementary feedback term 73 will always be of opposite sign as the first one tries to follow the shank segment velocity while the second ones tries to control the shank segment velocity.

The above described braking process has been found to be very efficient and robust to inter-subjects variability as well as properly fulfilling desired cyclical or non-cyclical locomotion tasks. Moreover, the reactive and self-adjusting nature of the braking process allows to greatly reduce dependency on locomotion portion, gait speed or user physiological parameters, with respect to other types of systems relying on position control. Such implementation of the Eccentric joint behavior class implicitly manages end-of-motion collisions in a way that is very adaptable to various locomotion tasks and shows very high synergy with the user due to its physiologically-compliant nature.

One indirect benefit associated with the use of such a braking process with respect to other approaches based on hardware mechanisms arise from the fact that the actuator 144 is used in a regenerating mode. Regeneration occurs in an electrical motor when torque and velocity are in opposite directions. In such a case, assuming that proper drive electronics are used, the motor starts acting as a generator and may be self-sufficient as far as power consumption is concerned. Implementation of the braking process herein defined then leads to a positive power balance, as mechanical work is generated without drawing any power from the power source of the motorized prosthetic and/or orthotic device 200. Furthermore, depending on the quantity of energy required to be dissipated using the braking process, i.e. depending on locomotion tasks, gait speed, user gait style and user physiological parameters, it may also be possible to generate more energy than what is required by the actuator's 144 motor to ensure satisfactory braking. Assuming that a suitable power supply architecture is used, for example the power supply described in U.S. Pat. No. 7,230,352 entitled "COMPACT POWER SUPPLY" by Bedard et al., it may then be possible to store the extra energy, which is not required by the actuator 144 motor in order to sustain braking, for later use. From a motorized prosthetic and/or orthotic device 200 perspective, this allows an increase in autonomy without any additional components.

Energy Injection Implementation

The fourth class of lower-limb joint behavior, the Concentric class, may be advantageously addressed through an energy injection implementation. The Concentric class of joint behavior occurs whenever the lower-limb joints of the motorized prosthetic and/or orthotic device 200 are used in order to generate mechanical power or inject energy to sustain overall gait. While some behaviors described above could be easily implemented on passive lower-limb prosthetic or orthotic joints, integration of a highly performing concentric behavior requires the availability of mechanical power generation capabilities at the joint. While it might be argued that the use of simple passive mechanical components, for example springs, accumulators, etc., may allow energy storing and return, the limitations in power generation capabilities with respect to specific gait requirements make it difficult to achieve something close to a reactive behavior using these passive mechanical components.

While obvious occurrence of Concentric joint behavior are found in locomotion tasks such as stairs ascent, incline plane ascent or sit-to-stand transfer, the implementation of the Concentric reactive behavior aims at fulfilling gait requirements different from the ones found in these locomotion tasks. The concentric joint behavior implemented as reactive behavior is related to the implementation of joint motion in order to enforce sufficient toe clearance in both cyclical and non-cyclical locomotion tasks.

Toe clearance management is an important feature of any motorized prosthetic and/or orthotic device 200, as this feature may dramatically influence the overall device usability. While multiple approaches exist regarding management of toe clearance on both passive and active lower-limb devices currently on the market, they all lack the ability to properly manage toe clearance for both cyclical and non-cyclical locomotion tasks, without affecting the device's usability or requiring the user to adopt specific behaviors, often leading to a pathological gait.

From that respect, the definition of a generalized joint behavior addressing the toe clearance management problem in a physiologically coherent and robust manner appears to be the most straightforward solution.

Concentric behavior targeting basic toe clearance management is then defined as a low-level reactive behavior allowing to connect sensory input from the sensors 142 to a pre-defined joint behavior. Upon detection of the motorized prosthetic and/or orthotic device 200 transition from the interacting 30 to the non-interacting 40 mechanical configuration (see FIGS. 3 and 4, respectively), energy injection at the joint level is triggered and takes place as a supplementary feed forward term in the formulation of the variable gains impedance controller's 70 of FIG. 7.

Since the requirements for any Concentric joint action targeting toe clearance are both user-specific and locomotion task specific, energy injection is advantageously implemented in conjunction with a user-interface device allowing the customization of the basic energy injection implementation's behavior. Through the combination of the energy injection implementation and associated user-interface device, it may be possible to define a general baseline behavior. In order to account for more complex concentric joint behavior requirements, it may be possible to couple this general baseline behavior with higher level inference engines that will allow the dynamic modification of the energy injection amplitude, timing and duration. Such modifications depend on the nature of the task currently performed by the user.

From an inference layer 120 perspective (see FIG. 1), three specializations are considered to affect the general baseline behavior of the energy injection implementation and are associated with sustaining adequate toe clearance and heel rise in level walking, stairs or incline ascent, and stairs or incline descent. Appropriate adjustment of the energy injection implementation reactive layer 130 parameters by the inference layer 120 engines may ensure fulfillment of these three specializations in a seamless manner.

Figure 9:
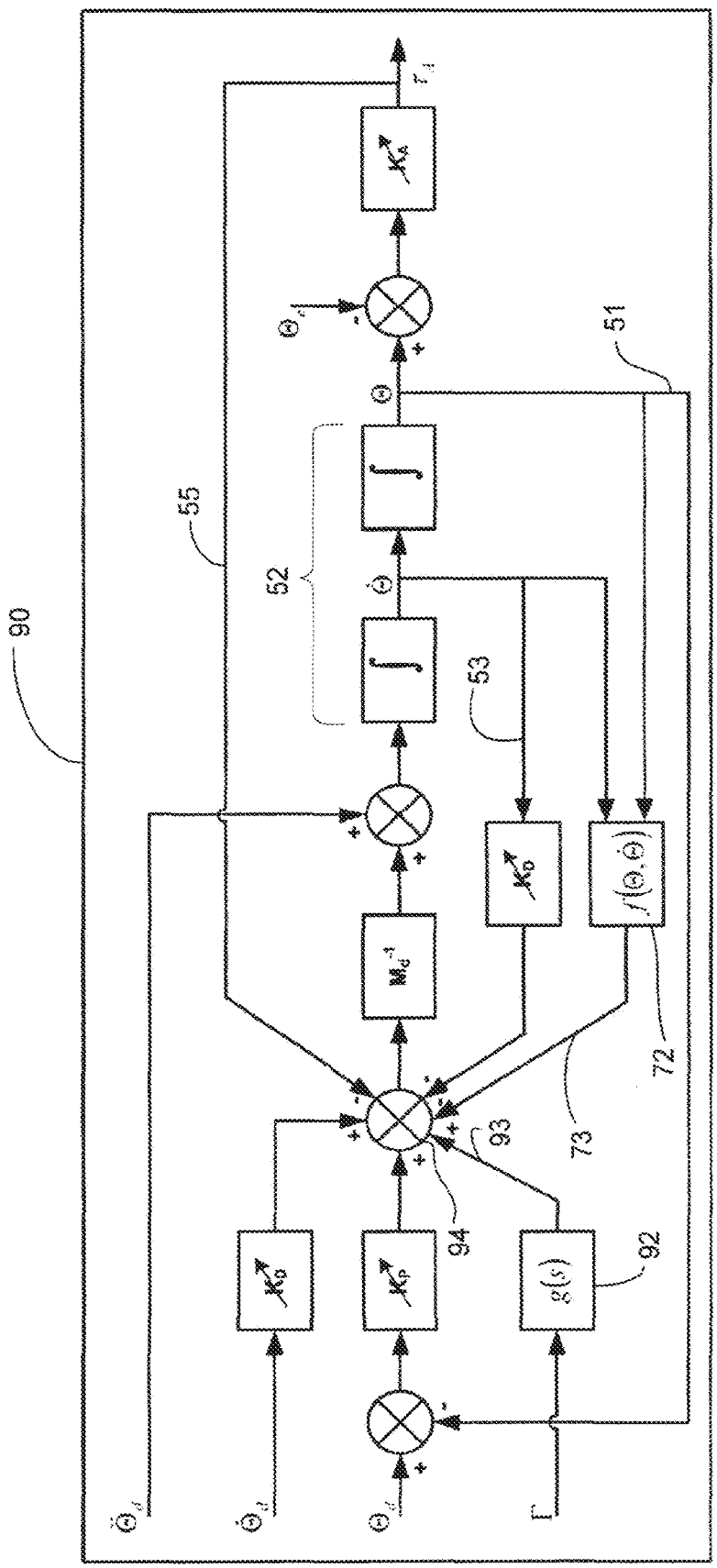
FIG. 9 is a block diagram of a variable gains impedance controller with energy injection feedforward function.

Referring to FIG. 9, from a variable gains impedance controller 90 standpoint, the energy injection implementation may be advantageously implemented as a feed forward transfer function 92 acting as a discrete pulse generator which directly injects a force pulse 93 at the output 94 of the positional terms of the variable impedance controller 90 upon triggering of the transfer function discrete input $\Gamma$. As discussed above, the triggering mechanism may consist in a low-level detection of the transition from the interacting configuration 30, i.e. foot in contact with the ground, to the non-interacting configuration 40, i.e. aerial lower-limb configuration. The feed forward transfer function 92, g(s), may take a wide variety of form, for example a pulse type waveform. Other types of discrete-time waveforms may also be defined for that specific purpose (e.g., saw tooth, exponential, etc.).

Hence, upon transition to the non-interacting configuration 40, both the energy injection and perturbation force matching 64 (see FIG. 6) are active, ensuring that minimal motorized prosthetic or orthotic apparatus 140 joint flexion take places before the joint is left in its minimal impedance state. While this last sequence of event takes place without consideration of the cyclical nature of the task being executed, more specific actions are expected to take place and sustain the complete swing phase of cyclical locomotion tasks, such that proper foot clearance and subsequent foot placement takes place.

While the benefits associated with the behavior described above for the cyclical locomotion tasks are quite straightforward, it is the capability to properly manage requirements associated with non-cyclical tasks that make the implementation of the concentric joint behavior interesting for a motorized prosthetic and/or orthotic device 200. Combination of the Concentric behavior allowing the enforcement of basic toe clearance in limited ambulation tasks to the Isometric behavior allowing support in the absence of motion during the contact phase without consideration of the knee flexion angle at which the ground contact occurs greatly eases the burden associated with the manipulation of a lower-limb motorized prosthetic and/or orthotic device 200 with respect to more conventional designs.

Moreover, it was shown in experimental testing that the combination of the energy injection implementation with the force matching and force rejection implementations greatly enhance the usability of the motorized prosthetic and/or orthotic device 200 when facing constrained environments, obstacles, or other types of situations that cannot be characterized through typical locomotion tasks. Enforcement of a certain knee flexion angle through the effects of the energy injection implementation also facilitates the implementation of less pathological gait habits in limited ambulation, as stance phase knee flexion is easily obtained and provide adequate support, without being overly stiff. Hence, improved physiological interaction between the user and its motorized prosthetic and/or orthotic device 200 may be obtained.

It is to be understood that the force matching and force rejection implementations, the braking implementation and the force injection implementation may be integrated individually or in any combination thereof into a conventional variable gains impedance controller to form a reactive layer control system for orthotic or prosthetic devices.

Although the present invention has been described by way of particular non-limiting illustrative embodiments and examples thereof, it should be noted that it will be apparent to persons skilled in the art that modifications may be applied to the present particular embodiment without departing from the scope of the present invention.

REFERENCES

[1] Hogan, N., *Impedance Control: An Approach to Manipulation: Part I—Theory*. ASME Journal of Dynamic Systems, Measurement and Controls, vol. 107, pp. 1-7, 1985.
[2] Hogan, N., *Impedance Control: An Approach to Manipulation: Part II—Implementation*, ASME Journal of Dynamic Systems, Measurement and Controls, vol. 107, pp. 8-16, 1985.
[3] Hogan, N., *Impedance Control: An Approach to Manipulation: Part III—Applications*, ASME Journal of Dynamic Systems, Measurement and Controls, vol. 107, pp. 17-24, 1985.

What is claimed is:

1. A system for controlling an apparatus, the system comprising:
   a force sensor;
   a torque sensor;
   a position sensor;
   an impedance controller configured to control a motorized prosthetic apparatus;
   and a processor in communication with the impedance controller, the force sensor, the position sensor, and the torque sensor, the processor configured to:
   receive a first signal from the force sensor, the first signal indicative of an interaction between the apparatus and ground;
   receive a second signal from the torque sensor, the second signal indicative of a torque at a joint;
   receive a third signal indicative of a position of the joint from the position sensor;
   determine a result by multiplying the second signal by a value, wherein the result is based on the first signal;
   and responsive to a determination that the first signal indicates an absence of the interaction between the apparatus and the ground, the processor is further configured to: multiply the second signal by a negative value and providing the result to the impedance controller;
   estimate a velocity of the joint from the third signal;
   multiply a difference between a velocity set-point and the estimated velocity by a velocity gain value and providing the result to the impedance controller;
   multiplying the difference between a position set-point and the third signal by a position gain value and providing the result to the impedance controller; and
   output a control signal to the actuator based at least in part on the force feedback, wherein the actuator adjusts joint resistance to motion based at least in part on the control signal.

2. The system of claim 1, wherein the value is a positive value and unitary when the first signal indicates a presence of the interaction between the apparatus and the ground, wherein the value is a negative value and unitary when the first signal indicates an absence of the interaction between the apparatus and the ground.

3. The system of claim 1, further comprising a position sensor, wherein the processor is further configured to:
   receive a third signal from the position sensor, the third signal indicative of a position of the joint; and
   responsive to the first signal indicating the interaction between the apparatus and the ground, the processor is further configured to:
   multiply the second signal by a positive value;
   estimate a velocity of the joint from the third signal;
   multiply a difference between a velocity set-point and the estimated velocity by a velocity gain value; and
   multiply a difference between a position set-point and the third signal by a position gain value.

4. The system of claim 1, wherein the processor is further configured to:
   provide a braking feedback value to the impedance controller based at least in part on a determination that the velocity is greater than a first threshold and the third signal indicative of position is greater than a second threshold, wherein the braking feedback value increases joint resistance to motion.

5. The system of claim 4, wherein the braking feedback value is based on a ratio of the velocity to a square of an indicated position offset with a motion stop target of the apparatus.

6. The system of claim 1, wherein the processor is further configured to provide a pulse to impedance controller based on a determination that the force sensor indicates a transition from the interaction between the apparatus and the ground to an absence of the interaction between the apparatus and the ground.

7. The system of claim 6, wherein the processor is further configured to dynamically adjust characteristics of the pulse, wherein the dynamically adjusted characteristics of the pulse include a combination of one or more of an amplitude, a duration, or a timing.

8. The system of claim 1, wherein the first signal is a measure of load at a shank portion of the motorized prosthetic apparatus, and wherein the interaction between the apparatus and the ground is determined by a single value hysteretic thresholding of the first signal received from the force sensor.

9. A system for controlling an apparatus, the system comprising:

a force sensor;
a torque sensor;
an impedance controller configured to control a motorized prosthetic apparatus;
and a processor in communication with the impedance controller, the force sensor, and the torque sensor, the processor configured to:
receive a first signal from the force sensor, the first signal indicative of an interaction between the apparatus and ground;
receive a second signal from the torque sensor, the second signal indicative of a torque at a joint;
receive a signal indicative of velocity of the joint; receive a signal indicative of position of the joint;
determine a result by multiplying the second signal by a value, wherein the result is based on the first signal;
and responsive to a determination that the first signal indicates an absence of the interaction between the apparatus and the ground, the processor is further configured:
multiply the second signal by a negative value and providing the result to the impedance controller,
multiply a difference between a velocity set-point and the signal indicative of velocity by a velocity gain value and providing the result to the impedance controller,
multiply a difference between a position set-point and the signal indicative of position by a position gain value and providing the result to the impedance controller; and
output a control signal to the actuator based at least in part on the force feedback, wherein the actuator adjusts joint resistance to motion based at least in part on the control signal.

10. A system for controlling an apparatus, the system comprising:
an impedance controller configured to control an actuator of an apparatus, wherein the impedance controller is further configured to:
receive a first signal indicative of a torque at a joint of the apparatus;
determine a torque feedback based at least in part on the first signal and a gain factor, wherein during swing phase the gain factor is a first gain factor, wherein during stance phase the gain factor is a second gain factor that is different from the first gain factor and wherein one of the first gain factor or the second gain factor is a positive value and the other one of the first gain factor or the second gain factor is a negative value; and
output a control signal to the actuator based at least in part on the torque feedback, wherein the actuator adjusts joint resistance to motion based at least in part on the control signal.

11. The system of claim 10, wherein the apparatus is a lower-limb prosthetic device.

12. The system of claim 10, wherein the actuator is coupled to a prosthetic limb member, and the actuator forms at least a portion of the joint of the apparatus.

13. The system of claim 10, wherein the impedance controller is further configured to receive a second signal indicative of a position of the joint, wherein the control signal is further based at least in part on the second signal.

14. The system of claim 10, further comprising a torque sensor, wherein the torque sensor produces the first signal.

15. The system of claim 10, wherein the impedance controller is further configured to receive a second signal indicative of an interaction between the apparatus and a walking surface.

16. The system of claim 15, wherein the control signal is further based at least in part on the second signal.

17. The system of claim 15, wherein the impedance controller is further configured to control the actuator to reduce joint resistance based at least in part on a determination that the second signal indicates an absence of interaction between the apparatus and the walking surface.

* * * * *